(12) United States Patent
Nazarenko et al.

(10) Patent No.: US 9,593,366 B2
(45) Date of Patent: Mar. 14, 2017

(54) INDIVIDUALLY SYNTHESIZED PRIMERS TO BE USED IN WHOLE GENOME AMPLIFICATION

(75) Inventors: Irina Nazarenko, Gaithersburg, MD (US); Dominic O'Neil, Hilden (DE); Ha Thai, Rockville, MD (US); Attila Lorincz, North Potomac, MD (US)

(73) Assignee: QIAGEN GAITHERSBURG, INC., Gaithersburg, MD (US)

( * ) Notice: Subject to any disclaimer, the term of this patent is extended or adjusted under 35 U.S.C. 154(b) by 1148 days.

(21) Appl. No.: 13/126,165

(22) PCT Filed: Oct. 26, 2009

(86) PCT No.: PCT/US2009/062062
§ 371 (c)(1),
(2), (4) Date: Jul. 12, 2011

(87) PCT Pub. No.: WO2010/056499
PCT Pub. Date: May 20, 2010

(65) Prior Publication Data
US 2011/0256591 A1  Oct. 20, 2011

Related U.S. Application Data

(60) Provisional application No. 61/109,745, filed on Oct. 30, 2008.

(51) Int. Cl.
*C12Q 1/68* (2006.01)
(52) U.S. Cl.
CPC .................. *C12Q 1/6844* (2013.01)
(58) Field of Classification Search
None
See application file for complete search history.

(56) References Cited

U.S. PATENT DOCUMENTS

| 5,043,272 | A | 8/1991 | Hartley | 435/91 |
| 6,124,120 | A | 9/2000 | Lizardi | 435/91.2 |
| 6,280,949 | B1 | 8/2001 | Lizardi | 435/6 |
| 6,617,137 | B2 | 9/2003 | Dean | 435/91.1 |
| 6,642,034 | B2 | 11/2003 | Lizardi | 435/91.1 |
| 6,977,148 | B2 | 12/2005 | Dean | 435/6 |
| 7,074,600 | B2 | 7/2006 | Dean | 435/91.2 |
| 7,297,485 | B2 | 11/2007 | Bornarth | 435/6 |
| 8,497,069 | B2 * | 7/2013 | Hutchison et al. | 435/6.12 |
| 2008/0057513 | A1 * | 3/2008 | Farrell | 435/6 |

FOREIGN PATENT DOCUMENTS

| EP | 09752575.2 | 10/2009 |
| WO | WO 99/18241 | 4/1999 |
| WO | PCT/US2009/062062 | 10/2009 |
| WO | WO 2010/056499 | 5/2010 |

OTHER PUBLICATIONS

Dean et al. (2001) Genome Research vol. 11: pp. 1095-1099.*
International Search Report mailed Feb. 16, 2010 for PCT/US2009/062062 filed on Oct. 26, 2009, which published as WO 2010/056499 on May 20, 2010 (Applicants—Qiagen GmBH; Inventors—Nazarenko et al.) (4 pages).
Written Opinion mailed Feb. 16, 2010 for PCT/US2009/062062 filed on Oct. 26, 2009, which published as WO 2010/056499 on May 20, 2010 (Applicants—Qiagen GmBH; Inventors—Nazarenko et al.) (6 pages).
International Preliminary Report on Patentability mailed May 3, 2011 for PCT/US2009/062062 filed on Oct. 26, 2009, which published as WO 2010/056499 on May 20, 2010 (Applicants—Qiagen GmBH; Inventors—Nazarenko et al.) (7 pages).
Response to Rule 161(1) and 162 EPC Communication filed Dec. 19, 2011 for EP Patent Application No. 09 75 2575.2, which claims priority to for PCT/US2009/062062 filed on Oct. 26, 2009 (Applicants—Qiagen GmBH; Inventors—Nazarenko et al.) (9 pages).
Rule 161(1) and 162 EPC Communication issued Jun. 15, 2011 for EP Patent Application No. 09 75 2575.2, which claims priority to for PCT/US2009/062062 filed on Oct. 26, 2009 (Applicants—Qiagen GmBH; Inventors—Nazarenko et al.) (3 pages).
Amended Claims filed May 25, 2011 for EP Patent Application No. 09 75 2575.2, which claims priority to for PCT/US2009/062062 filed on Oct. 26, 2009 (Applicants—Qiagen GmBH; Inventors—Nazarenko et al.) (3 pages).
Bannai M, et al. (2004) Single-nucleotide-polymorphism genotyping for whole-genome-amplified samples using automated fluorescence correlation spectroscopy. Anal Biochem. 327(2): 215-221.
Birkenmeyer LG, et al. (1991) DNA probe amplification methods. J Virol Methods. 35(2): 117-126.
Cheung VG, et al. (1996) Whole genome amplification using a degenerate oligonucleotide primer allows hundreds of genotypes to be performed on less than one nanogram of genomic DNA. Proc Natl Acad Sci USA. 93(25): 14676-14679.
Dean FB, et al. (2001) Rapid amplification of plasmid and phage DNA using Phi 29 DNA polymerase and multiply-primed rolling circle amplification. Genome Res. 11(6): 1095-1099.
Dean FB, et al. (2002) Comprehensive human genome amplification using multiple displacement amplification Proc Natl Acad Sci USA. 99(8): 5261-5266.
Detter JC, et al. (2002) Isothermal strand-displacement amplification applications for high-throughput genomics. Genomics. 80(6): 691-698.
Dhulipala PDK, et al. (2003) GenomiPhi Amplification of Human Genomic DNA: Utility of Amplified DNA in Genetic Variation Experiments. FASEB J., Fed. Amer. Soc. for Exp. Biol. 17: 4-5. Abstract No. 371.3.
Esteban JA, et al. (1993) Fidelity of phi 29 DNA polymerase. Comparison between protein-primed initiation and DNA polymerization. J Biol Chem. 268(4): 2719-2726.
Lage JM, et al. (2003) Whole genome analysis of genetic alterations in small DNA samples using hyperbranched strand displacement amplification and array-CGH. Genome Res. 13(2): 294-307.
Landegren U. (1993) Molecular mechanics of nucleic acid sequence amplification. Trends Genet. 9(6): 199-204.
Lizardi PM, et al. (1998) Mutation detection and single-molecule counting using isothermal rolling-circle amplification. Nat Genet. 19(3): 225-232.

(Continued)

*Primary Examiner* — Aaron Priest
(74) *Attorney, Agent, or Firm* — Ballard Spahr LLP

(57) ABSTRACT

Disclosed are compositions and methods for random amplification of nucleic acid sequences of interest using random-G-deficient primers. Also disclosed are methods of randomly amplifying a target nucleic acid sequence using random G-deficient primers alone or in combination with random, partially random, or specific primers.

23 Claims, 4 Drawing Sheets

(56) References Cited

OTHER PUBLICATIONS

Lockhart DJ, et al. (1996) Expression monitoring by hybridization to high-density oligonucleotide arrays. Nat Biotechnol. 14(13): 1675-1680.

Luthra R, et al. (2004) Isothermal multiple displacement amplification: a highly reliable approach for generating unlimited high molecular weight genomic DNA from clinical specimens. J Mol Diagn. 6(3): 236-242.

Nelson JR, et al. (2002) TempliPhi, phi29 DNA polymerase based rolling circle amplification of templates for DNA sequencing. Biotechniques. Suppl: 44-47.

Telenius H, et al. (1992) Degenerate oligonucleotide-primed PCR: general amplification of target DNA by a single degenerate primer. Genomics. 13(3): 718-725.

* cited by examiner

Figure 4.

| 48 Sequences | | | | 96 Sequences | | |
|---|---|---|---|---|---|---|
| Conc. | MFI (200 Copies) | %CV | | Conc. | MFI (200 Copies) | %CV |
| 50µM | 670 | 34% | | 50µM | 1312 | 13% |
| 150µM | 1563 | 1% | | 150µM | 1463 | 4% |
| 250µM | 1522 | 10% | | 250µM | 1716 | 2% |

| 48 Sequences | | | | 96 Sequences | | |
|---|---|---|---|---|---|---|
| Conc. | MFI (200 Copies) | %CV | | Conc. | MFI (200 Copies) | %CV |
| 150µM | 2284 | 4% | | 150µM | 2490 | 1% |
| 250µM | 2473 | 2% | | 250µM | 2150 | 4% |
| 350µM | 1625 | 62% | | 350µM | 287 | 102% |

INDIVIDUALLY SYNTHESIZED PRIMERS TO BE USED IN WHOLE GENOME AMPLIFICATION

CROSS REFERENCE TO RELATED APPLICATIONS

The present application is a National Phase Application of International Application No. PCT/US2009/062062, filed Oct. 26, 2009, which claims priority to U.S. Provisional Patent Application No. 61/109,745, filed on Oct. 30, 2008, each of which is herein incorporated by reference in its entirety.

FIELD OF THE INVENTION

The disclosed invention is generally in the field of nucleic acid amplification.

BACKGROUND OF THE INVENTION

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods,* 35:117-126 (1991); Landegren, *Trends Genetics* 9:199-202 (1993)).

Fundamental to most genetic analysis is availability of genomic DNA of adequate quality and quantity. Since DNA yield from human samples is frequently limiting, much effort has been invested in general methods for propagating and archiving genomic DNA. Methods include the creation of EBV-transformed cell lines or whole genome amplification (WGA) by random or degenerate oligonucleotide-primed PCR. Whole genome PCR, a variant of PCR amplification, involves the use of random or partially random primers to amplify the entire genome of an organism in the same PCR reaction. This technique relies on having a sufficient number of primers of random or partially random sequence such that pairs of primers will hybridize throughout the genomic DNA at moderate intervals. Replication initiated at the primers can then result in replicated strands overlapping sites where another primer can hybridize. By subjecting the genomic sample to multiple amplification cycles, the genomic sequences will be amplified. Whole genome PCR has the same disadvantages as other forms of PCR. However, WGA methods suffer from high cost or insufficient coverage and inadequate average DNA size (Telenius et al., *Genomics.* 13:718-725 (1992); Cheung and Nelson, *Proc Natl Acad Sci USA.* 93:14676-14679 (1996); Zhang et al., *Proc Natl Acad Sci USA.* 89:5847-5851 (1992)).

Another field in which amplification is relevant is RNA expression profiling, where the objective is to determine the relative concentration of many different molecular species of RNA in a biological sample. Some of the RNAs of interest are present in relatively low concentrations, and it is desirable to amplify them prior to analysis. It is not possible to use the polymerase chain reaction to amplify them because the mRNA mixture is complex, typically consisting of 5,000 to 20,000 different molecular species. The polymerase chain reaction has the disadvantage that different molecular species will be amplified at different rates, distorting the relative concentrations of mRNAs.

Some procedures have been described that permit moderate amplification of all RNAs in a sample simultaneously. For example, in Lockhart et al., *Nature Biotechnology* 14:1675-1680 (1996), double-stranded cDNA was synthesized in such a manner that a strong RNA polymerase promoter was incorporated at the end of each cDNA. This promoter sequence was then used to transcribe the cDNAs, generating approximately 100 to 150 RNA copies for each cDNA molecule. This weak amplification system allowed RNA profiling of biological samples that contained a minimum of 100,000 cells. However, there is a need for a more powerful amplification method that would permit the profiling analysis of samples containing a very small number of cells.

Another form of nucleic acid amplification, involving strand displacement, has been described in U.S. Pat. No. 6,124,120 to Lizardi. In one form of the method, two sets of primers are used that are complementary to opposite strands of nucleotide sequences flanking a target sequence. Amplification proceeds by replication initiated at each primer and continuing through the target nucleic acid sequence, with the growing strands encountering and displacing previously replicated strands. In another form of the method a random set of primers is used to randomly prime a sample of genomic nucleic acid. The primers in the set are collectively, and randomly, complementary to nucleic acid sequences distributed throughout nucleic acid in the sample. Amplification then proceeds by replication initiating at each primer and continuing so that the growing strands encounter and displace adjacent replicated strands. In another form of the method concatenated DNA is amplified by strand displacement synthesis with either a random set of primers or primers complementary to linker sequences between the concatenated DNA. Synthesis proceeds from the linkers, through a section of the concatenated DNA to the next linker, and continues beyond, with the growing strands encountering and displacing previously replicated strands.

Another form of nucleic acid amplification is whole genome amplification using DNA polymerases. For example, whole genome amplification using DNA polymerases is described in U.S. Pat. Nos. 6,977,148; 6,617,137; 7,074,600; 7,297,485; 6,124,120; 6,280,949; and 6,642,034. In some of the whole genome amplification reactions, φ29 DNA polymerase is used. In some of the reactions of whole genome amplification using φ29 DNA polymerase, the reaction proceeds efficiently with short, non-specific primers that contain phosphorothioate linkages at the 3' end. Commercially available φ29 amplification kits, such as GenomiPhi (GE Healthcare UK Ltd, Buckinghamshire, England), have used random phosphorothioated hexamers for primers, and are the most prevalent primer design for WGA applications. These random primers are synthesized as a random mixture. While random primers provide efficient amplification by allowing multiple priming events to occur, there are some problems with their synthesis. Most importantly, it is nearly impossible to gather good quality control information, and the material is subject to lot-to-lot variability between syntheses. An object of the present invention is to replace the random synthesis with a controlled synthesis leading to more consistent results without compromising sensitivity or any of the advantages of using random primer amplification.

BRIEF SUMMARY OF THE INVENTION

Disclosed herein is a method of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands.

Also disclosed is a method of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein nucleic acids in the target sample are not separated from other material in the target sample. Further disclosed is a method of randomly amplifying messenger RNA, the method comprising, reverse transcribing messenger RNA to produce a first strand cDNA, bringing into contact a set of random G-deficient primers, DNA polymerase, and the first strand cDNA, and incubating under conditions that promote replication of the first strand cDNA, wherein replication of the first strand cDNA results in replicated strands, wherein during replication at least one of the replicated strands is displaced from the first strand cDNA by strand displacement replication of another replicated strand.

Disclosed is a method of randomly amplifying a target nucleic acid sequence, the method comprising: (a) mixing a set of random G-deficient primers with a target sample, to produce a primer-target sample mixture, and incubating the primer-target sample mixture under conditions that promote hybridization between the random G-deficient primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity.

Also disclosed is a method of randomly amplifying a whole genome, the method comprising, bringing into contact a set of random G-deficient primers, DNA polymerase, and a target sample, and incubating the target sample under conditions that promote replication of the target sequence.

BRIEF DESCRIPTION OF THE DRAWINGS

FIG. 2 also shows the analytical sensitivity of random G-deficient primers is comparable to random primers.

FIG. 4 shows optimal concentrations of random G-deficient primers.

DETAILED DESCRIPTION OF THE INVENTION

Figure 1:
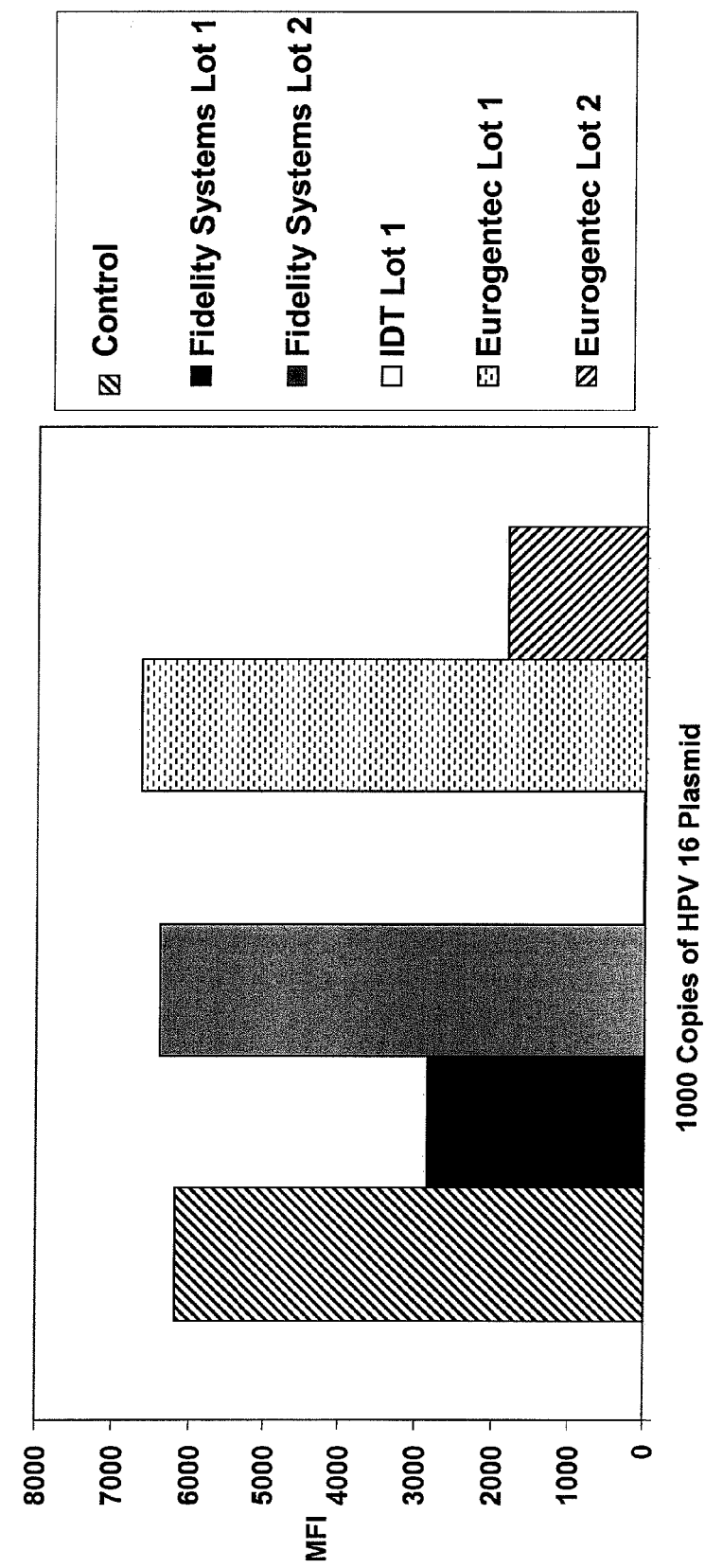
FIG. 1 shows a graphic representation of the performance of 50 μm scale synthesis primers from three vendors. The comparison showed inconsistent results. The inconsistency is seen between lots produced by different vendors and among lots produced from the same vendor
Figure 2:
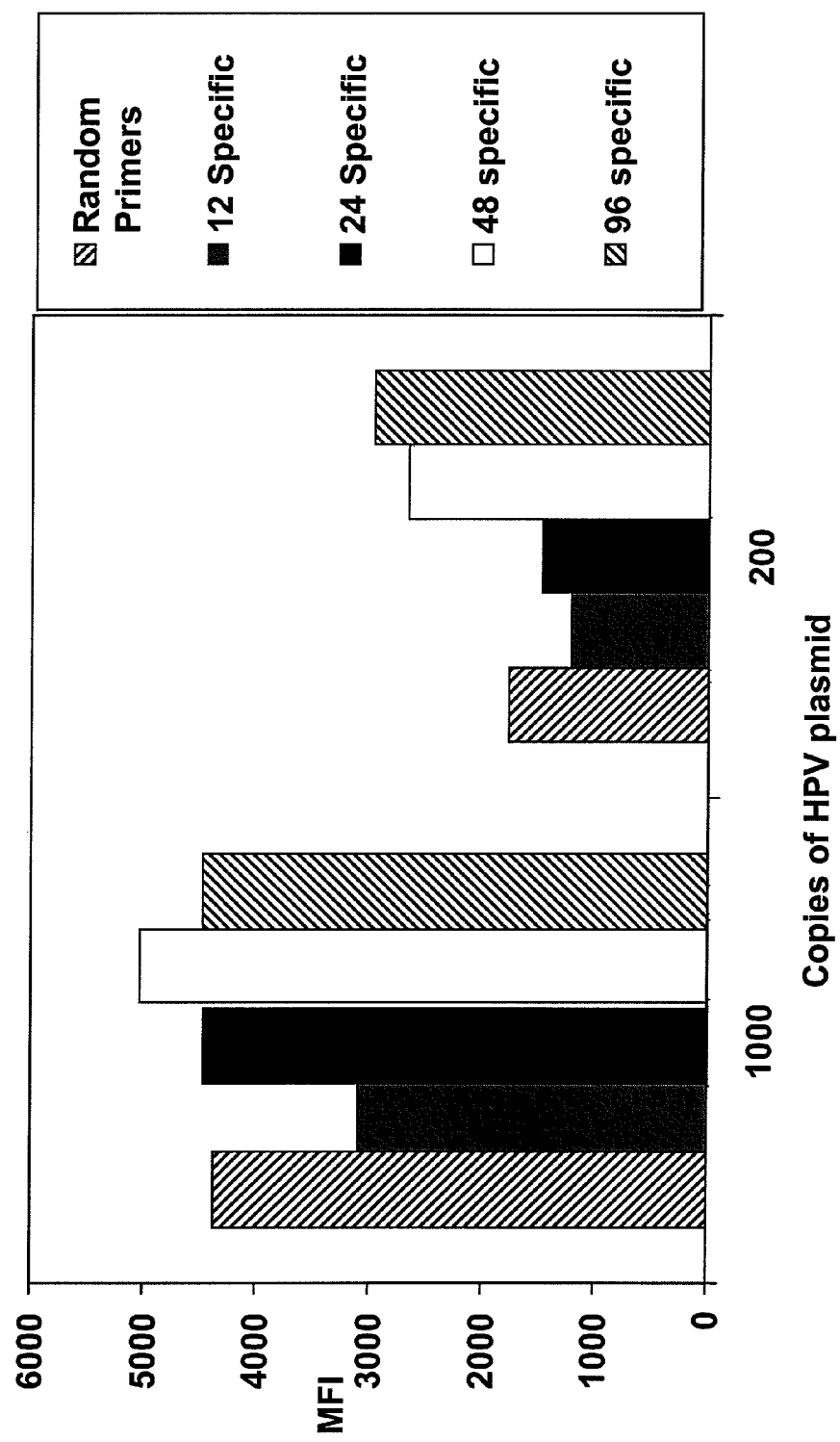
FIG. 2 shows the random G-deficient primers perform comparably to random primers.
Figure 3:
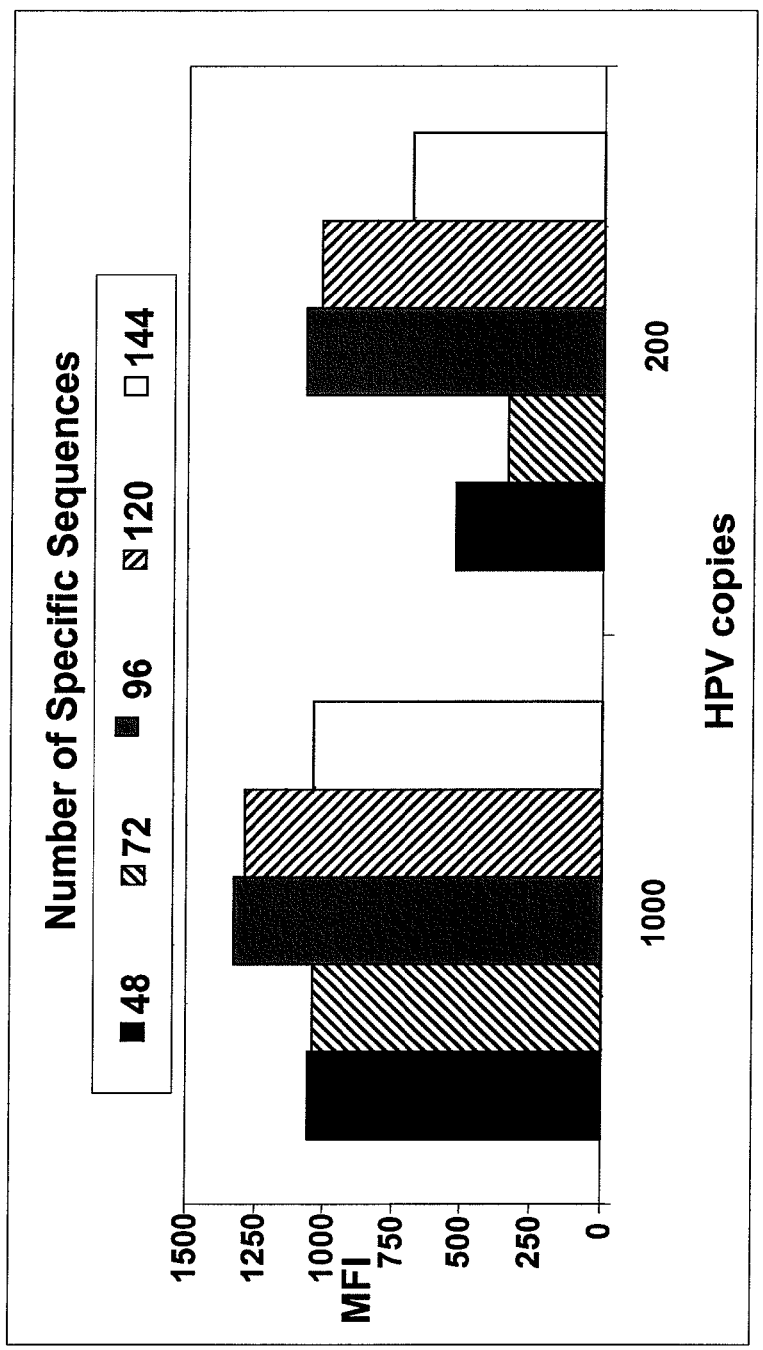
FIG. 3 shows efficient amplification achieved with random G-deficient primers mixes of 48 to 144 specific sequences.

Before the present compounds, compositions, articles, devices, and/or methods are disclosed and described, it is to be understood that the aspects described below are not limited to specific synthetic methods or to particular reagents unless otherwise, as such may, of course, vary. It is also to be understood that the terminology used herein is for the purpose of describing particular aspects only and is not intended to be limiting.

All patents, patent applications and publications cited herein, whether supra or infra, are hereby incorporated by reference in their entireties into this application in order to more fully describe the state of the art as known to those skilled therein as of the date of the invention described and claimed herein.

A. GENERAL DESCRIPTION

Disclosed herein are compositions and methods for random amplification of nucleic acid sequences of interest. It has been discovered that synthesis of random oligonucleotides and their use in whole genome amplification can be problematic and lead to inefficient amplification. For example, it have been discovered that large scale synthesis of the short random DNA oligonucleotides used in prior methods produces the most inconsistent results. These findings have led to the discovery that replacing the random synthesis of oligonucleotides with a partially controlled synthesis of individual oligonucleotides allows for better quality control of the primer synthesis production which in turn leads to more consistent results without compromising sensitivity or any of the advantages of using random primer amplification. Specifically, while random primers provide efficient amplification by allowing multiple priming events to occur, there are some problems with their synthesis. Most importantly, it is nearly impossible to gather good quality control information, and the material is subject to lot-to-lot variability between syntheses. Replacing the random synthesis with a controlled synthesis of individual oligonucleotides (random G-deficient primers) is disclosed herein. Using random G-deficient primers allows for better control of the primer synthesis production leading to more consistent results without compromising sensitivity or any of the advantages of using random primer amplification. For example, for a 5-base (pentamer) primer there are 1024 possible sequences that can be generated and thus for a random primer mix of pentamers there can be in theory 1024 different primers in the mix. The examples below show that the use of random G-deficient primers will amplify with efficiency equal to or greater than using a random primer mix. Random G-deficient primers can be synthesized and combined in equal proportions to generate a mix of primers that will give optimal efficiency of amplification. As such, disclosed herein are methods of randomly amplifying a target nucleic acid sequence using random G-deficient primers alone or in combination with random, partially random, or specific primers.

1. Definitions and Nomenclature

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

The word "or" as used herein means any one member of a particular list and also includes any combination of members of that list.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

"Optional" or "optionally" means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

Materials

A. Target Sequence

The target sequence, which is the object of amplification, can be any nucleic acid. The target sequence can include multiple nucleic acid molecules, such as in the case of whole genome amplification, multiple sites in a nucleic acid molecule, or a single region of a nucleic acid molecule. For multiple strand displacement amplification, the target sequence can be a single region or multiple sites in a nucleic acid molecule or nucleic acid sample. For whole genome amplification, the target sequence is the entire genome or nucleic acid sample. A target sequence can be in any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwash, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one or more different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, forensic samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

For multiple strand displacement amplification, target sequences can be those which are difficult to amplify using PCR due to, for example, length or composition. For whole genome amplification, target sequences can be nucleic acid samples from a single cell. For multiple strand displacement amplification of concatenated DNA the target is the concatenated DNA. The target sequence can be either one or both strands of cDNA. The target sequences for use in the disclosed method can be part of nucleic acid molecules or samples that are complex and non-repetitive (with the exception of the linkers in linker-concatenated DNA and sections of repetitive DNA in genomic DNA).

Target nucleic acids can include damaged DNA and damaged DNA samples. For example, preparation of genomic DNA samples can result in damage to the genomic DNA (for example, degradation and fragmentation). This can make amplification of the genome or sequences in it both more difficult and provide less reliable results (by, for example, resulting in amplification of many partial and fragmented genomic sequences. Damaged DNA and damaged DNA samples are thus useful for the disclosed method of amplifying damaged DNA. Any degraded, fragmented or otherwise damaged DNA or sample containing such DNA can be used in the disclosed method.

1. Target Sequences for Multiple Strand Displacement Amplification

Multiple sites in a nucleic acid sample can be amplified simultaneously in the same MSDA reaction, however, a single nucleic acid sequence of interest can also be amplified in a MSDA reaction. This sequence(s) to be amplified are referred to below as a target sequence(s). It is preferred that a target sequence(s) for MSDA include two types of target regions, an amplification target and a hybridization target. The hybridization target includes the sequences in the target sequence that are complementary to the primers in a set of primers. The amplification target is the portion of the target sequence which is to be amplified. The amplification target can be all, or a substantial portion of the sample or target molecule. The amplification target can be downstream of, or flanked by the hybridization target(s). There is no specific sequence or structural requirements for choosing a target sequence. The hybridization target and the amplification target within the target sequence are defined in terms of the relationship of the target sequence to the primers in a set of primers. The primers can be designed to match the chosen target sequence or random, degenerate, or random G-deficient primers can be used in this method. Although preferred, it is not required that sequences to be amplified and the sites of hybridization of the primers be separate since sequences in and around the sites where the primers hybridize will be amplified.

In multiple strand displacement amplification of circularized DNA, the circular DNA fragments can be the amplification targets. The hybridization targets include the sequences that are complementary to the primers used for amplification. One form of circular DNA for amplification is circularized cDNA.

In multiple strand displacement amplification of linker-concatenated DNA, the DNA fragments joined by the linkers are the amplification targets and the linkers can be the hybridization target. The hybridization targets (that is, the linkers) include the sequences that are complementary to the primers used for amplification. One form of concatenated DNA for amplification is concatenated cDNA.

B. SAMPLES

Nucleic acid molecules, which are the object of amplification, can be any nucleic acid from any source. In general, the disclosed methods can be performed using a sample that contains (or is suspected of containing) nucleic acid molecules to be amplified. Samples containing, or suspected of containing, nucleic acid molecules can also be referred to as nucleic acid samples. Samples, such as nucleic acid samples can comprise target sequences. Cell and tissue samples are a form of nucleic acid sample. Samples for use in the disclosed methods can also be samples that are to be tested for the presence of nucleic acids (that is, samples that may or may not contain nucleic acids). For whole genome amplification, the sample can be all or a substantial portion of an entire genome. As used herein, a substantial portion of a genome refers to the presence of 90% or more of the sequences present in the entire genome. A sample, such as a nucleic acid sample or genomic nucleic acid sample, including or comprising a substantial portion of a genome refers to a sample including 90% or more of the sequences present in the entire genome. A genomic nucleic acid sample refers to any sample derived from genomic nucleic acids and including or comprising a notable portion of the entire genome. As used herein, a notable portion of a genome refers to the presence of 20% or more of the sequences present in the entire genome. A sample, such as a nucleic acid sample or genomic nucleic acid sample, including or comprising a notable portion of a genome refers to a sample including 20% or more of the sequences present in the entire genome. As used herein, a significant portion of a genome refers to the presence of 50% or more of the sequences present in the entire genome. A sample, such as a nucleic acid sample or genomic nucleic acid sample, including or comprising a significant portion of a genome refers to a sample including 50% or more of the sequences present in the entire genome. A genomic nucleic acid sample is a form of nucleic acid sample and a form of sample. Reference herein to a sample encompasses nucleic acid samples and genomic samples unless the context clearly indicates otherwise. Reference herein to a nucleic acid sample encompasses genomic nucleic acid samples unless the context clearly indicates otherwise.

A sample can comprise a genome, and the genome can comprise any fraction of the nucleic acids in the sample. The genome can comprise, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of the nucleic acids in the sample.

The nucleic acids in a sample need not be pure to be amplified in the disclosed methods. Some forms of the disclosed methods are useful for amplifying impure nucleic acid samples, such as crude cell lysates. The nucleic acids in a sample or in a stabilized or neutralized sample can be, for example, less than 0.01% pure, less than 0.5% pure, less than 0.1% pure, less than 0.2% pure, less than 0.4% pure, less than 0.6% pure, less than 0.8% pure, less than 1% pure, less than 2% pure, less than 3% pure, less than 4% pure, less than 5% pure, less than 6% pure, less than 8% pure, less than 10% pure, less than 15% pure, less than 20% pure, less than 25% pure, less than 30% pure, less than 40% pure, or less than 50% pure by weight excluding water.

A nucleic acid sample can be any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample comprising or derived from one or more eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwash, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. Types of useful nucleic acid samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, forensic samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

It has been discovered that it is unnecessary to have prior knowledge of whether or not a sample contains amplifiable nucleic acids. Some forms of the disclosed methods can be employed to test whether or not a sample suspected of containing nucleic acids actually does contain nucleic acids. Production of amplified DNA from such samples using the disclosed method is evidence that the sample contained nucleic acids. More generally, practice of the disclosed methods does not require any knowledge of any nucleic acid sequence in a sample. Thus, the disclosed methods can be used to amplify nucleic acids from any source, regardless of a lack of specific sequence information. This is in contrast to other amplification methods, such as PCR, where it is necessary to have prior information of at least a portion of the nucleic acid sequences believed to be present in the sample in order to perform the amplification. In this instance, the PCR amplification reaction will fail if the nucleic acids present in the sample are different from the expected sample nucleic acids. If a sample contains a mixture of nucleic acids, then nucleic acids of the appropriate type alone will be amplified in a PCR reaction, but not the other types of nucleic acids. In contrast, the disclosed methods provide for amplification of most or all of the nucleic acids present in the sample. The disclosed methods are equally adaptable to using samples that conventionally are not expected or believed to contain nucleic acids. For instance, serum or plasma from humans or other higher animals were believed to not contain free host nucleic acids. However, it was discovered that the disclosed methods could amplify nucleic acids present in such samples.

For whole genome amplification, nucleic acid samples can be nucleic acid samples from a single cell. The nucleic acid samples can also be nucleic acid molecules and samples that are complex and non-repetitive. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome. The target genome is preferably pure or substantially pure, but this is not required. For example, a genomic sample from an animal source can include nucleic acid from contaminating or infecting organisms.

The nucleic acid sample can be, or can be derived from, for example, one or more whole genomes from the same or different organisms, tissues, cells or a combination; one or more partial genomes from the same or different organisms, tissues, cells or a combination; one or more whole chromosomes from the same or different organisms, tissues, cells or a combination; one or more partial chromosomes from the same or different organisms, tissues, cells or a combination; one or more chromosome fragments from the same or different organisms, tissues, cells or a combination; one or more artificial chromosomes; one or more yeast artificial chromosomes; one or more bacterial artificial chromosomes; one or more cosmids; or any combination of these.

Where the nucleic acid sample is a nucleic acid sample of high complexity, the nucleic acid molecules in the sample can be from any source or combination of sources that result in a highly complex sample. By high complexity or high sequence complexity is meant that the nucleic acid sample has a large number of unique (that is, non-repeated) sequences. The total number of nucleotides in the unique sequences is the sequence complexity of the nucleic acid sample. For example, the human genome has approximately $3\times10^9$ unique sequences and so has a sequence complexity of approximately $3\times10^9$ nucleotides. A nucleic acid sample of high sequence complexity has a sequence complexity of at least $1\times10^6$ nucleotides. Thus, a nucleic acid sample of high sequence complexity can have, for example, a sequence complexity of at least $1\times10^6$ nucleotides, a sequence complexity of at least $1\times10^7$ nucleotides, a sequence complexity of at least $1\times10^8$ nucleotides, or a sequence complexity of at least $1\times10^9$ nucleotides.

The nucleic acid sample can also be a nucleic acid sample of significant complexity. By significant complexity or significant sequence complexity is meant that the nucleic acid sample has a significant number of unique (that is, non-repeated) sequences. A nucleic acid sample of significant sequence complexity has a sequence complexity of at least $1\times10^5$ nucleotides. Thus, a nucleic acid sample of significant sequence complexity can have, for example, a sequence complexity of at least $1\times10^5$ nucleotides, a sequence complexity of at least $1\times10^6$ nucleotides, a sequence complexity of at least $1\times10^7$ nucleotides, a sequence complexity of at least $1\times10^8$ nucleotides, or a sequence complexity of at least $1\times10^9$ nucleotides. The nucleic acid sample can also be a nucleic acid sample of notable complexity. By notable complexity or notable sequence complexity is meant that the nucleic acid sample has a notable number of unique (that is, non-repeated) sequences. A nucleic acid sample of notable sequence complexity has a sequence complexity of at least $1\times10^4$ nucleotides. Thus, a nucleic acid sample of significant sequence complexity can have, for example, a sequence complexity of at least $1\times10^4$ nucleotides, a sequence complexity of at least $1\times10^5$ nucleotides, a sequence complexity of at least $1\times10^6$ nucleotides, a sequence complexity of at least $1\times10^7$ nucleotides, a sequence complexity of at least $1\times10^8$ nucleotides, or a sequence complexity of at least $1\times10^9$ nucleotides.

Nucleic acid samples and genomic nucleic acid samples can have, for example, a sequence complexity of at least $1\times10^3$ nucleotides, a sequence complexity of at least $1\times10^4$ nucleotides, a sequence complexity of at least $1\times10^5$ nucleotides, a sequence complexity of at least $1\times10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

Samples can be used and manipulated in the disclosed methods. For example, a sample can be exposed to alkaline conditions or brought into contact or mixed with a lysis solution or denaturing solution. As used herein, the term sample refers both to source samples, samples used in the disclosed methods in whole, and to portions of source samples used in the disclosed methods. Thus, for example, a portion of a source sample that is exposed to alkaline conditions is considered to be a sample itself. All or a portion of a sample can be exposed to alkaline conditions or brought into contact or mixed with a lysis solution or denaturing solution. Similarly, the pH of all or a portion of a sample exposed to alkaline conditions or brought into contact or mixed with a lysis solution or denaturing solution can be reduced, or all or a portion of a sample exposed to alkaline conditions or brought into contact with a lysis solution or denaturing solution can be brought into contact or mixed with a stabilization solution. All or a portion of the resulting stabilized or neutralized sample can be incubated under conditions that promote replication of nucleic acids. An amplification mixture can comprise all or a portion of a stabilized or neutralized sample. An amplification mixture is the reaction solution where nucleic acids are amplified.

C. PRIMERS

Primers for use in the disclosed amplification methods are oligonucleotides having sequence complementary to the target sequence. This sequence is referred to as the complementary portion of the primer. The complementary portion of a primer can be any length that supports specific and stable hybridization between the primer and the target sequence under the reaction conditions. Generally, for reactions at 37° C., this can be 10 to 35 nucleotides long or 16 to 24 nucleotides long. For whole genome amplification, the primers can be from 5 to 60 nucleotides long, and in particular, can be 5, 6, 7, 8, 9, 10, 11, 12, 13, 14, 15, 16, 17, 18, 19, and/or 20 nucleotides long.

Specific, random, degenerate, and random G-deficient primers can be used in the disclosed methods. For example, primers can be specifically designed to hybridize to a specific sequence. Such primers are referred to simply as primers or as specific primers. Specific primers can be used when the sequence of the target sequence is known and can also be specifically designed as such. Degenerate primers can also be used in the disclosed methods. "Degenerate primers" refers to specific primer in which one or more of, but less than the total number of nucleotide positions, is occupied by a base selected at random from among a complete set of possibilities, but commonly limited to the four nucleosides, dAMP, dCMP, dGMP, or dTMP.

Primers can also be randomly synthesized without reference to a target sequence. Such primers are referred to as random primers as they are randomly synthesized without reference to a target sequence. Random primers have been used in prior amplification methods where the sequence of the target sequence is unknown. Specifically, random primers are oligonucleotides in which each of the nucleotide positions is occupied by a base selected at random from among a complete set of possibilities, but commonly limited to the four nucleosides, dAMP, dCMP, dGMP, or dTMP. For example, for a 5-base (pentamer) random primer there are 1024 possible sequences that can be generated and thus for a random primer mix of pentamers there can be in theory 1024 different primers in the mix.

In addition, random G-deficient primers can be used in the disclosed methods. Random G-deficient primers are random primers that are synthesized without reference to the target nucleic acid sequence and have one or both of the following traits: (1) do not comprise three or more consecutive guanine (G) residues and (2) do not comprise two or more consecutive guanine residues at the 3' end. For example, as described above for a 5-base (pentamer) random primer there are 1024 possible sequences that can be generated, however for random G-rich primers there are only 115 possible sequences that can be generated and thus for a random primer mix of pentamers there can be in theory 909 different primers in the mix.

For some forms of the disclosed methods, such as those using primers of random, degenerate, or random G-deficient sequence (that is, use of a collection of primers having a variety of sequences), primer hybridization need not be specific. In such cases the primers need only be effective in priming synthesis. For example, in whole genome amplification specificity of priming is not essential since the goal generally is to amplify all sequences equally. Sets of random, degenerate, or random G-deficient can be composed of primers 5, 6, 7, 8, 9, 10, 11, 12, 13, 14, 15, 16, 17, 18, 19, and/or 20 nucleotides long or more. Primers of five or six nucleotides long are referred to as pentamer and hexamer primers, respectively. For example, primers for whole genome amplification can be random G-deficient pentamer primers, for example, random G-deficient pentamer primers. Similarly, sets of random G-deficient primers of other particular lengths, or of a mixture of lengths preferably contain every possible sequence the length of the primer, or, in particular, the length of the complementary portion of the primer with the exception that the primers do not comprise three or more consecutive guanine (G) residues and/or do not comprise two or more consecutive guanine residues at the 3' end.

The disclosed primers can have one or more modified nucleotides. For example, primers in a primer set that can be used in the disclosed methods can each contain at least one modified nucleotide. The at least one modified nucleotide in the primers disclosed herein can render the primers resistant to 3'-5' exonuclease.

Such primers are referred to herein as modified primers. Modified primers have several advantages. First, some forms of modified primers, such as RNA/2'-O-methyl RNA chimeric primers, have a higher melting temperature (Tm) than DNA primers. This increases the stability of primer hybridization and will increase strand invasion by the primers. This can lead to more efficient priming. Also, since the primers are made of RNA, they will be exonuclease resistant. Such primers, if tagged with minor groove binders at their 5' end, will also have better strand invasion of the template dsDNA. In addition, RNA primers can also be very useful for whole genome amplification (WGA) of nucleic acid(s) from biological samples such as cells or tissue. Since the biological samples contain endogenous RNA, this RNA can be degraded with RNase to generate a pool of random oligomers, which can then be used to prime the polymerase for amplification of the DNA. This can eliminate the need to add primers to the reaction. Alternatively, DNase digestion of biological samples can generate a pool of DNA oligo primers for RNA dependent DNA amplification.

Chimeric primers can also be used. Chimeric primers are primers having at least two types of nucleotides, such as both deoxyribonucleotides and ribonucleotides, ribonucleotides and modified nucleotides, or two different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. The DNA and RNA portions of such primers can have random or degenerate sequences. Other forms of chimeric primers are, for example, 5'-(2'-O-Methyl) RNA-RNA-3' or 5'-(2'-O-Methyl) RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Primers composed, either in whole or in part, of nucleotides with universal bases are useful for reducing or eliminating amplification bias against repeated sequences in a target sample. This could be useful, for example, where a loss of sequence complexity in the amplified products is undesirable. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in their entirety for their teaching of base modifications.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)nO]m CH$_3$, —O(CH$_2$)nOCH$_3$, —O(CH$_2$)nNH$_2$, —O(CH$_2$)nCH$_3$, —O(CH$_2$)n-ONH$_2$, and —O(CH$_2$)nON[(CH$_2$)nCH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'O-methyl ribonucleotides; about 50% or more of the nucleotides can be ribonucleotides, 2'43'-methyl ribonucleotides, or a mixture of ribonucleotides and 2'-O-methyl ribonucleotides; or all of the nucleotides are ribonucleotides, 2'O-methyl ribonucleotides, or a mixture of ribonucleotides and 2'-O-methyl ribonucleotides. The nucleotides can be comprised of bases (that is, the base portion of the nucleotide) and can (and normally will) comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Primers may, but need not, also contain additional sequence at the 5' end of the primer that is not complementary to the target sequence. This sequence is referred to as the non-complementary portion of the primer. The non-complementary portion of the primer, if present, serves to facilitate strand displacement during DNA replication. The non-complementary portion of the primer can also include a functional sequence such as a promoter for an RNA polymerase. The non-complementary portion of a primer may be any length, but is generally 1 to 100 nucleotides long, and preferably 4 to 8 nucleotides long. The use of a non-complementary portion is not preferred when random or partially random primers are used for whole genome amplification.

1. Primers for Whole Genome Strand Displacement Amplification

In the case of whole genome strand displacement amplification (WGSDA), a set of primers having random or partially random nucleotide sequences can be used. By "partially random" is meant that one or more of the nucleotides is not random, i.e., at least one specific nucleotide (selected from the list disclosed herein) was inserted in a given position in the nucleotide sequence intentionally. In addition, a set of random G-deficient primers can be used for whole genome strand displacement amplification. In a nucleic acid sample of significant or substantial complexity, which is the preferred target sequence for WGSDA, specific nucleic acid sequences present in the sample need not be known and the primers need not be designed to be complementary to any particular sequence. Rather, the complexity of the nucleic acid sample results in a large number of different hybridization target sequences in the sample which will be complementary to various random, partially random, or random G-deficient primers. The complementary portion of primers for use in WGSDA can be fully randomized, have only a portion that is randomized, or be otherwise selectively randomized.

The number of random base positions in the complementary portion of primers can be from 20% to 100% of the total number of nucleotides in the complementary portion of the primers. The number of random base positions can also be from 30% to 100% of the total number of nucleotides in the complementary portion of the primers. The number of random base positions can also be from 50% to 100% of the total number of nucleotides in the complementary portion of the primers. Sets of primers random or partially random sequences can be synthesized using standard techniques by allowing the addition of any nucleotide at each position to be randomized. The sets of primers can also be composed of primers of similar length and/or hybridization characteristics.

A set of primers can include any desired number of primers of different or the same nucleotide sequence. For example, a set of random G-deficient primers can be any number of primers with different sequences. For whole genome strand displacement amplification, a set of primers can include a plurality of primers. For example, a set of primers include 25 or more, 50 or more, 100 or more, 200 or more, 400 or more, 800 or more, or 1000 or more primers. In addition a set of random G-deficient pentamer primers can include 909 different primers. In general, the more primers used, the greater the level of amplification that will be obtained. There is no fundamental upper limit to the number of primers that a set of primers can have. However, for a given target sequence, the number of primers in a set of primers will generally be limited to the number of hybridization sites available in the target sequence. For example, use of 48 different strategically chosen random G-deficient pentamers can amplify with efficiency equal to or greater than using a random primer mix with 1024 different random primers. Any combination of the preferred upper and lower limits for the number of primers in a set of primers described above are specifically contemplated, including all intermediate ranges.

2. Primers for Multiple Strand Displacement Amplification

In the case of multiple strand displacement amplification, the complementary portion of each primer can be designed to be complementary to the hybridization target in the target sequence, however, random, degenerate, or random G-deficient primers can also be used in multiple strand displacement amplification where the complementary portion of each primer is synthesized without reference to the target sequence. In a set of primers, the complementary portion of each primer can be complementary to a different portion of the target sequence. The primers in the set can also be complementary to adjacent sites in the target sequence. Such adjacent sites in the target sequence can also be adjacent to the amplification target in the target sequence. A set of random, partially random and random G-deficient primers can also be used and that the set of primers will randomly hybridize to the target sequence in a similar manner as described above.

When hybridized to a target sequence, the primers in a set of primers can be separated from each other. When hybridized, the primers in a set of primers can be separated from each other by at least 5 bases. In addition, when hybridized, the primers in a set of primers can be separated from each other by at least 10, 20, 30, 40 or 50 bases. It is also possible that, when hybridized, the primers in a set of primers are separated from each other by no more than about 500, 400, 300, or 200 bases. Any combination of the upper and lower limits of separation described above are specifically contemplated, including all intermediate ranges. The primers in a set of primers need not, when hybridized, be separated from each other by the same number of bases.

The optimal separation distance between primers will not be the same for all DNA polymerases, because this parameter is dependent on the net polymerization rate. A processive DNA polymerase will have a characteristic polymerization rate which may range from 5 to 300 nucleotides per second, and may be influenced by the presence or absence of accessory ssDNA binding proteins and helicases. In the case of a non-processive polymerase, the net polymerization rate will depend on the enzyme concentration, because at higher concentrations there are more re-initiation events and thus the net polymerization rate will be increased. An example of a processive polymerase is $\phi$29 DNA polymerase, which proceeds at 50 nucleotides per second. An example of a non-processive polymerase is Vent exo(-) DNA polymerase, which will give effective polymerization rates of 4 nucleotides per second at low concentration, or 16 nucleotides per second at higher concentrations.

To obtain an optimal yield in an MSDA reaction, the primer spacing can be adjusted to suit the polymerase being used. Long primer spacing can be employed when using a polymerase with a rapid polymerization rate. Shorter primer spacing can be employed when using a polymerase with a slower polymerization rate.

A set of primers can include any desired number of primers of different nucleotide sequence. For MSDA, a set of primers can include a plurality of primers. For example, a set of primers include 3 or more, 4 or more, 5 or more, 6 or more, or 7 or more primers. In general, the more primers used, the greater the level of amplification that will be obtained. There is no fundamental upper limit to the number of primers that a set of primers can have. However, for a given target sequence, the number of primers in a set of primers will generally be limited to the number of hybridization sites available in the target sequence. For example, if the target sequence is a 10,000 nucleotide DNA molecule and 20 nucleotide primers are used, there are 500 non-overlapping 20 nucleotide sites in the target sequence. Even more primers than this could be used if overlapping sites are either desired or acceptable. As such, a set of primers can include no more than about 300 primers, no more than about 200 primers, no more than about 100 primers, or no more than about 50 primers. A set of primers can also include from 7 to about 50 primers. Any combination of the upper and lower limits for the number of primers in a set of primers described above are specifically contemplated, including all intermediate ranges.

3. Detection Tags

The non-complementary portion of a primer can include sequences to be used to further manipulate or analyze amplified sequences. An example of such a sequence is a detection tag, which is a specific nucleotide sequence present in the non-complementary portion of a primer. Detection tags have sequences complementary to detection probes. Detection tags can be detected using their cognate detection probes. Detection tags become incorporated at the ends of amplified strands. The result is amplified DNA having detection tag sequences that are complementary to the complementary portion of detection probes. If present, there may be one, two, three, or more than three detection tags on a primer. In one example, a primer can have one, two, three or four detection tags. In another example, a primer can have 10 detection tags or less. There is no fundamental limit to the number of detection tags that can be present on a primer except the size of the primer. When there are multiple detection tags, they may have the same sequence or they may have different sequences, with each different sequence complementary to a different detection probe. For example, a primer can contain detection tags that have the same sequence such that they are all complementary to a single detection probe. For some multiplex detection methods, it is primers can contain up to six detection tags and that the detection tag portions have different sequences such that each of the detection tag portions is complementary to a different detection probe, for example. A similar effect can be achieved by using a set of primers where each has a single different detection tag. The detection tags can each be any length that supports specific and stable hybridization between the detection tags and the detection probe. For this purpose, a length of 10 to 35 nucleotides can be used, with a detection tag portion 15 to 20 nucleotides long being a specific example.

4. Address Tag

Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. A primer can have one or two address tags. In one example, a primer can have 10 address tags or less. There is no fundamental limit to the number of address tags that can be present on a primer except the size of the primer. When there are multiple address tags, they may have the same sequence or they may have different sequences, with each different sequence complementary to a different address probe. For example, a primer can contain address tags that have the same sequence such that they are all complementary to a single address probe. The address tag portion can be any length that supports specific and stable hybridization between the address tag and the address probe. For this purpose, a length between 10 and 35 nucleotides long can be used, with an address tag portion 15 to 20 nucleotides long being a specific example.

D. LYSIS SOLUTION

In the disclosed method, the cells can be exposed to alkaline conditions by mixing the cells with a lysis solution. A lysis solution is generally a solution that can raise the pH of a cell solution sufficiently to cause cell lysis. Denaturing solutions can be used as lysis solutions so long as the denaturing solution can have the effects required of lysis solutions. In some embodiments, the lysis solution can comprises a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of lysis solution include lysis solution comprising 400 mM KOH, lysis solution comprising 400 mM KOH and 10 mM EDTA, lysis solution comprising 400 mM KOH, 100 mM dithiothreitol, and 10 mM EDTA, and lysis solution consisting of 400 mM KOH, 100 mM dithiothreitol, and 10 mM EDTA. Other useful formulations of lysis solution include lysis solution comprising 100 mM KOH, lysis solution comprising 100 mM KOH and 2.5 mM EDTA, lysis solution comprising 100 mM KOH, 25 mM dithiothreitol, and 2.5 mM EDTA, and lysis solution consisting of 100 mM KOH, 25 mM dithiothreitol, and 2.5 mM EDTA. Useful lysis solutions can have a pH of 8. Lysis solutions can be diluted prior to use. In such cases, the amount of lysis solution added to a reaction generally could be increased proportionally.

In some embodiments, the lysis solution can comprise a plurality of basic agents. As used herein, a basic agent is a compound, composition or solution that results in alkaline conditions. In some embodiments, the lysis solution can comprise a buffer. Useful buffers include phosphate buffers, "Good" buffers (such as BES, BILINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The lysis solution can comprise a plurality of buffering agents. As used herein, a buffering agent is a compound, composition or solution that acts as a buffer. An alkaline buffering agent is a buffering agent that results in alkaline conditions. In some embodiments, the lysis solution can comprise a combination of one or more bases, basic agents, buffers and buffering agents.

The amount of lysis solution mixed with the cells can be that amount that causes a substantial number of cells to lyse or those that cause a sufficient number of cells to lyse. Generally, this volume will be a function of the pH of the cell/lysis solution mixture. Thus, the amount of lysis solution to mix with cells can be determined generally from the volume of the cells and the alkaline concentration of the lysis buffer. For example, a smaller volume of a lysis solution with a stronger base and/or higher concentration of base would be needed to create sufficient alkaline conditions than the volume needed of a lysis solution with a weaker base and/or lower concentration of base. The lysis solution can be formulated such that the cells are mixed with an equal volume of the lysis solution (to produce the desired alkaline conditions). Lysis solutions are well known in the art and any lysis solution can be used in the methods disclosed herein. For example, lysis solutions can be solutions that have a pH of about 8.0, about 8.5, about 9.0, about 9.5, about 10.0, about 10.5, about 11.0, about 11.5, about 12.0, about 12.5, or about 13.0.

Lysis solutions can have, for example, component concentrations of about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

Final concentrations of lysis solution components (after mixing with samples) can be, for example, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The lysis solution can be composed of multiple solutions and/or components that can be added to cells separately or combined in different combinations prior to addition to cells. Thus, for example, a solution of 400 mM KOH and 10 mM EDTA and a solution of 100 mM dithiothreitol can be added to the cells separately. Similarly, the disclosed kits can be composed of multiple solutions and/or components to be combined to form a lysis solution prior to addition to cells or for separate addition to cells. Stock lysis solutions can be diluted to form final lysis solutions for use in the disclosed method. Stock lysis solutions can have any concentration described herein for lysis solutions or any concentration that is more concentrated than any lysis solution or lysis solution concentration described herein. The final concentration of lysis solution components (after mixing with samples) can be any concentration described herein for lysis solutions. Useful final concentrations of lysis solution components can be 50 mM KOH, 12.5 mM dithiothreitol, and 1.25 mM EDTA.

E. STABILIZATION SOLUTION

In the disclosed method, the pH of the cell lysate or sample can be reduced to form a stabilized or neutralized cell lysate or stabilized or neutralized sample. A stabilization solution is generally a solution that can reduce the pH of a cell lysate or sample exposed to alkaline conditions as described elsewhere herein. In some embodiments, the stabilization solution can comprise an acid. Useful acids include hydrochloric acid, sulfuric acid, phosphoric acid, acetic acid, acetylsalicylic acid, ascorbic acid, carbonic acid, citric acid, formic acid, nitric acid, perchloric acid, HF, HBr, $H_1$, $H_2S$, HCN, HSCN, HClO, monochloroacetic acid, dichloroacetic acid, trichloroacetic acid, and any carboxylic acid (ethanoic, propanoic, butanoic, etc., including both linear or branched chain carboxylic acids). In some embodiments, the stabilization solution can comprise a buffer. Useful buffers include Tris-HCl, HEPES, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. Useful formulations of stabilization solutions include stabilization solution comprising 800 mM Tris-HCl; stabilization solution comprising 800 mM Tris-HCl at pH 4.1, and stabilization solution consisting of 800 mM Tris-HCl, pH 4.1. Useful formulations of stabilization solutions include stabilization solution comprising 800 mM Tris-HCl at pH 4, and stabilization solution consisting of 800 mM Tris-HCl, pH 4. Other useful formulations of stabilization solutions include stabilization solution comprising 160 mM Tris-HCl; stabilization solution comprising 160 mM Tris-HCl at pH 4.1, and stabilization solution consisting of 160 mM Tris-HCl, pH 4.1. Other useful formulations of stabilization solutions include stabilization solution comprising 160 mM Tris-HCl; stabilization solution comprising 160 mM Tris-HCl at pH 4, and stabilization solution consisting of 160 mM Tris-HCl, pH 4. Stabilization solutions can be diluted prior to use. In such cases, the amount of stabilization solution added to a reaction generally could be increased proportionally.

In some embodiments, the stabilization solution can comprise a plurality of acidic agents. As used herein, an acidic agent is a compound, composition or solution that forms an acid in solution. In some embodiments, the stabilization solution can comprise a plurality of buffering agents. An acidic buffering agent is a buffering agent that forms an acid in solution. In some embodiments, the stabilization solution can comprise a combination of one or more acids, acidic agents, buffers and buffering agents.

A stabilized cell lysate or stabilized samples is a cell lysate or sample the pH of which is in the neutral range (from about pH 6.0 to about pH 9.0). Useful stabilized cell lysates and samples have a pH that allows replication of nucleic acids in the cell lysate. For example, the pH of the stabilized cell lysate or sample is usefully at a pH at which the DNA polymerase can function. The pH of the cell lysate or sample can be reduced by mixing the cell lysate or sample with a stabilization solution.

The amount of stabilization solution mixed with the cell lysate or sample can be that amount that causes a reduction in pH to the neutral range (or other desired pH value). Generally, this volume will be a function of the pH of the cell lysate/stabilization solution mixture or of the sample/stabilization solution mixture. Thus, the amount of stabilization solution to mix with the cell lysate or sample can be determined generally from the volume of the cell lysate or sample, its pH and buffering capacity, and the acidic concentration of the stabilization buffer. For example, a smaller volume of a stabilization solution with a stronger acid and/or higher concentration of acid would be needed to reduce the pH sufficiently than the volume needed of a stabilization solution with a weaker acid and/or lower concentration of acid. The stabilization solution can be formulated such that the cell lysate or sample is mixed with an equal volume of the stabilization solution (to produce the desired pH). For example, stabilization solutions can be solutions that have a pH of about 1.0, about 2.0, about 2.5, about 3.0, about 3.5, about 4.0, about 4.5, about 5.0, about 5.5, or about 6.0.

Stabilization solutions can have, for example, component concentrations of about 100 mM, about 200 mM, about 300 mM, about 400 mM, about 500 mM, about 600 mM, about 700 mM, about 800 mM, about 900 mM, or about 1 M. Final concentrations of stabilization solution components can be, for example, about 100 mM, about 200 mM, about 300 mM, about 400 mM, about 500 mM, about 600 mM, about 700 mM, about 800 mM, about 900 mM, or about 1 M.

The stabilization solution can be composed of multiple solutions and/or components that can be added to cell lysates and samples separately or combined in different combinations prior to addition to cell lysates and samples. Thus, for example, a solution of a buffer and a solution of an acid can be added to the cells separately. Similarly, the disclosed kits can be composed of multiple solutions and/or components to be combined to form a stabilization solution prior to addition to cell lysates or samples or for separate addition to cell lysates or samples. Stock stablization solutions can be diluted to form final stabilization solutions for use in the disclosed method. Stock stabilization solutions can have any concentration described herein for stabilization solutions or any concentration that is more concentrated than any stabilization solution or stabilization solution concentration described herein. The final concentration of stabilization solution components (after mixing with samples) can be any concentration described herein for stabilization solutions. Useful final concentrations of lysis solution components can be 80 mM Tris-HCl.

As used herein, a neutralization solution is a form of stabilization solution. Reference to neutralized cell lysates, neutralized sample, and other neutralized components or solutions is considered the equivalent of a stabilized cell lysate, stabilized sample, or other stabilized component or solution.

F. DENATURING SOLUTION

In some forms of the disclosed method, the DNA samples can be exposed to denaturing conditions by mixing the sample with a denaturing solution. A denaturing solution is generally a solution that can raise the pH of a sample sufficiently to cause, in combination with other conditions such as heating, substantial denaturation of DNA in the DNA sample. Substantial denaturation refers to denaturation of 90% or more of the nucleotides in 90% or more of the DNA molecules in a sample. In this context, denaturation of nucleotides refers to unpaired nucleotides whether physically denatured by treatment or already unpaired in the sample. Lysis solutions can be used as denaturing solutions so long as the lysis solution has the effects required of denaturing solutions.

In some embodiments, the denaturing solution can comprises a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of denaturing solution include denaturing solution comprising about 150 mM to about 500 mM NaOH, denaturing solution comprising about 150 mM to about 500 mM NaOH, and denaturing solution consisting of about 150 mM to about 500 mM NaOH. Denaturing solutions can be diluted prior to use. In such cases, the amount of denaturing solution added to a reaction generally could be increased proportionally.

In some embodiments, the denaturing solution can comprise a plurality of basic agents. As used herein, a basic agent is a compound, composition or solution that results in denaturing conditions. In some embodiments, the denaturing solution can comprise a buffer. Useful buffers include phosphate buffers, "Good" buffers (such as BES, BICINE, CAPS, EPPS, HEPES, MES, MOPS, PIPES, TAPS, TES, and TRIUNE), sodium cacodylate, sodium citrate, triethylammonium acetate, triethylammonium bicarbonate, Tris, Bis-tris, and Bis-tris propane. The denaturing solution can comprise a plurality of buffering agents. As used herein, a buffering agent is a compound, composition or solution that acts as a buffer. An alkaline buffering agent is a buffering agent that results in alkaline conditions. In some embodiments, the denaturing solution can comprise a combination of one or more bases, basic agents, buffers and buffering agents.

The amount of denaturing solution mixed with the DNA samples can be that amount that causes, in combination with other conditions such as heating, substantial denaturation of DNA in the DNA sample. Generally, this volume will be a function of the pH, ionic strength, and temperature of the sample/denaturing solution mixture. Thus, the amount of denaturing solution to mix with DNA samples can be determined generally from the volume of the DNA sample, the alkaline concentration of the denaturing buffer, and the temperature to which the resulting mixture will be heated. For example, at a given temperature, a smaller volume of a denaturing solution with a stronger base and/or higher concentration of base would be needed to create sufficient denaturing conditions than the volume needed of a denaturing solution with a weaker base and/or lower concentration of base. The denaturing solution can be formulated such that the DNA samples are mixed with, for example, one tenth volume of the denaturing solution (to produce the desired denaturing conditions). For example, denaturing solutions can be solutions that have a pH of about 9.0, about 9.5, about 10.0, about 10.5, about 11.0, about 11.5, about 12.0, about 12.5, or about 13.0. Denaturing solutions can have, for example, component concentrations of about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The denaturing solution can be composed of multiple solutions and/or components that can be added to DNA samples separately or combined in different combinations prior to addition to DNA samples. Thus, for example, a solution of a buffer and a solution of a base can be added to the samples separately. Similarly, the disclosed kits can be composed of multiple solutions and/or components to be combined to form a denaturing solution prior to addition to DNA samples or for separate addition to samples. Stock denaturing solutions can be diluted to form final denaturing solutions for use in the disclosed method. Stock denaturing solutions can have any concentration described herein for denaturing solutions or any concentration that is more concentrated than any denaturing solution or denaturing solution concentration described herein. The final concentration of denaturing solution components (after mixing with samples) can be any concentration described herein for denaturing solutions.

G. NUCLEIC ACID FINGERPRINTS

The disclosed method can also be used to produce replicated strands that serve as a nucleic acid fingerprint of a complex sample of nucleic acid. Such a nucleic acid fingerprint can be compared with other, similarly prepared nucleic acid fingerprints of other nucleic acid samples to allow convenient detection of differences between the samples. The nucleic acid fingerprints can be used both for detection of related nucleic acid samples and comparison of nucleic acid samples. For example, the presence or identity of specific organisms can be detected by producing a nucleic acid fingerprint of the test organism and comparing the resulting nucleic acid fingerprint with reference nucleic acid fingerprints prepared from known organisms. Changes and differences in gene expression patterns can also be detected by preparing nucleic acid fingerprints of mRNA from different cell samples and comparing the nucleic acid fingerprints. The replicated strands can also be used to produce a set of probes or primers that is specific for the source of a nucleic acid sample. The replicated strands can also be used as a library of nucleic acid sequences present in a sample. Nucleic acid fingerprints can be made up of, or derived from, whole genome amplification of a sample such that the entire relevant nucleic acid content of the sample is substantially represented, or from multiple strand displacement amplification of selected target sequences within a sample.

Nucleic acid fingerprints can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of nucleic acid fingerprints include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from nucleic acid fingerprints and replicated strands produced in the disclosed method can also be collected, used, saved, stored, and/or archived.

Nucleic acid fingerprints can also contain or be made up of other information derived from the information generated in the disclosed method, and can be combined with information obtained or generated from any other source. The informational nature of nucleic acid fingerprints produced using the disclosed method lends itself to combination and/or analysis using known bioinformatics systems and methods.

Nucleic acid fingerprints of nucleic acid samples can be compared to a similar nucleic acid fingerprint derived from any other sample to detect similarities and differences in the samples (which is indicative of similarities and differences in the nucleic acids in the samples). For example, a nucleic acid fingerprint of a first nucleic acid sample can be compared to a nucleic acid fingerprint of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and *Salmonella*. A different type of tissue refers to tissues of different types such as liver and kidney, or skin and brain. A different strain or species of organism refers to organisms differing in their species or strain designation as those terms are understood in the art.

H. SOLID-STATE DETECTORS

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including tubes, test tubes, eppendorf tubes, vessels, micro vessels, plates, wells, wells of micro well plates, wells of microtitre plates, chambers, micro fluidics chambers, micro machined chambers, sealed chambers, holes, depressions, dimples, dishes, surfaces, membranes, microarrays, fibers, glass fibers, optical fibers, woven fibers, films, beads, bottles, chips, compact disks, shaped polymers, particles and microparticles. A chip is a rectangular or square small piece of material. Surfaces and other reaction chambers can be sealable. Preferred forms for solid-state substrates are thin films, beads, or chips.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a multiplex assay, address probes specific for numerous different amplified nucleic acids (each representing a different target sequence amplified via a different set of primers) can be immobilized in an array, each in a different location. Capture and detection will occur only at those array locations corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (Mosk) (USSR) 25:718-730 (1991). A method for immobilization of 3'-amine oligonucleotides on casein-coated slides is described by Stimpson et al., *Proc. Natl. Acad. Sci. USA* 92:6379-6383 (1995). A preferred method of attaching oligonucleotides to solid-state substrates is described by Guo et al., *Nucleic Acids Res.* 22:5456-5465 (1994). Examples of nucleic acid chips and arrays, including methods of making and using such chips and arrays, are described in U.S. Pat. No. 6,287,768, U.S. Pat. No. 6,288,220, U.S. Pat. No. 6,287,776, U.S. Pat. No. 6,297,006, and U.S. Pat. No. 6,291,193.

I. SOLID-STATE SAMPLES

Solid-state samples are solid-state substrates or supports to which target sequences or MDA products (that is, replicated strands) have been coupled or adhered. Target sequences are preferably delivered in a target sample or assay sample. A preferred form of solid-state sample is an array sample. An array sample is a solid-state sample to which multiple different target sequences have been coupled or adhered in an array, grid, or other organized pattern.

Solid-state substrates for use in solid-state samples can include any solid material to which target sequences can be coupled or adhered. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including tubes, test tubes, eppendorf tubes, vessels, micro vessels, plates, wells, wells of micro well plates, wells of microtitre plates, chambers, micro fluidics chambers, micro machined chambers, sealed chambers, holes, depressions, dimples, dishes, surfaces, membranes, microarrays, fibers, glass fibers, optical fibers, woven fibers, films, beads, bottles, chips, compact disks, shaped polymers, particles and microparticles. A chip is a rectangular or square small piece of material. Surfaces and other reaction chambers can be sealable. Preferred forms for solid-state substrates are thin films, beads, or chips.

Target sequences immobilized on a solid-state substrate allow formation of target-specific amplified nucleic acid localized on the solid-state substrate. Such localization provides a convenient means of washing away reaction components that might interfere with subsequent detection steps, and a convenient way of assaying multiple different samples simultaneously. Amplified nucleic acid can be independently formed at each site where a different sample is adhered. For immobilization of target sequences or other oligonucleotide molecules to form a solid-state sample, the methods described above can be used. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

A preferred form of solid-state substrate is a glass slide to which up to 256 separate target samples have been adhered as an array of small dots. Each dot is preferably from 0.1 to 2.5 mm in diameter, and most preferably around 2.5 mm in diameter. Such microarrays can be fabricated, for example, using the method described by Schena et al., Science 270: 487-470 (1995). Briefly, microarrays can be fabricated on poly-L-lysine-coated microscope slides (Sigma) with an arraying machine fitted with one printing tip. The tip is loaded with 1 µl of a DNA sample (0.5 mg/ml) from, for example, 96-well microtiter plates and deposited ~0.005 µl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

J. DETECTION LABELS

To aid in detection and quantitation of nucleic acids amplified using the disclosed method, detection labels can be directly incorporated into amplified nucleic acids or can be coupled to detection molecules. For example, amplification products can be detected directly by, for example, primary labeling or secondary labeling, as described below. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

i. Primary Labeling

Primary labeling consists of incorporating labeled moieties, such as fluorescent nucleotides, biotinylated nucleotides, digoxygenin-containing nucleotides, or bromodeoxyuridine, during strand displacement replication. For example, one may incorporate cyanine dye deoxyuridine analogs (Yu et al., Nucleic Acids Res., 22:3226-3232 (1994)) at a frequency of 4 analogs for every 100 nucleotides. A preferred method for detecting nucleic acid amplified in situ is to label the DNA during amplification with BrdUrd, followed by binding of the incorporated BrdU with a biotinylated anti-BrdU antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.). Other methods for detecting nucleic acid amplified in situ include labeling the DNA during amplification with 5-methylcytosine, followed by binding of the incorporated 5-methylcytosine with an antibody (Sano et al., Biochim. Biophys. Acta 951:157-165 (1988)), or labeling the DNA during amplification with aminoallyl-deoxyuridine, followed by binding of the incorporated aminoallyl-deoxyuridine with an Oregon Green® dye (Molecular Probes, Eugene, Oreg.) (Henegariu et al., Nature Biotechnology 18:345-348 (2000)).

Another method of labeling amplified nucleic acids is to incorporate 5-(3-aminoallyl)-dUTP (AAdUTP) in the nucleic acid during amplification followed by chemical labeling at the incorporated nucleotides. Incorporated 5-(3-aminoallyl)-deoxyuridine (AAdU) can be coupled to labels that have reactive groups that are capable of reacting with amine groups. AAdUTP can be prepared according to Langer et al. (1981). Proc. Natl. Acad. Sci. USA. 78: 6633-37. Other modified nucleotides can be used in analogous ways. That is, other modified nucleotides with minimal modification can be incorporated during replication and labeled after incorporation.

Examples of labels suitable for addition to AAdUTP are radioactive isotopes, fluorescent molecules, phosphorescent molecules, enzymes, antibodies, and ligands. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Other fluorescent labels for use in the methods disclosed herein include, but are not limited to, fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4', 5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076. Labeled nucleotides can also be used as detection labels since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labelling. Cy3.5 and Cy7 are available as avidin or antidigoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

ii. Secondary Labeling with Detection Probes

Secondary labeling consists of using suitable molecular probes, referred to as detection probes, to detect the amplified nucleic acids. For example, a primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand.

iii. Multiplexing and Hybridization Array Detection

Detection of amplified nucleic acids can be multiplexed by using sets of different primers, each set designed for amplifying different target sequences. Only those primers that are able to find their targets will give rise to amplified products. There are two alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the target sequence as an address tag.

iv. Enzyme-Linked Detection

Amplified nucleic acid labeled by incorporation of labeled nucleotides can be detected with established enzyme-linked detection systems. For example, amplified nucleic acid labeled by incorporation of biotin using biotin-16-UTP (Roche Molecular Biochemicals) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

K. DETECTION PROBES

Detection tags specific for primers are disclosed above. Detection tags can also be used in non-primer nucleic acid sequences. Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnol.* 14:303-309 (1995)). The use of such probes eliminates the need for removal of unhybridized probes prior to label detection because the unhybridized detection probes will not produce a signal. This is especially useful in multiplex assays.

L. ADDRESS PROBES

An address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

M. OLIGONUCLEOTIDE SYNTHESIS

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et al. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. No. 6,294,664 and U.S. Pat. No. 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

N. DNA POLYMERASES

DNA polymerases useful in multiple displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Examples of strand displacement DNA polymerases include, but are not limited to bacteriophage φ29 DNA polymerase (U.S. Pat. Nos. 5,198,543 and 5,001,050 to Blanco et al.), Bst large fragment DNA polymerase (Exo(−) Bst; Aliotta et al., *Genet. Anal.* (Netherlands) 12:185-195 (1996)) and exo(−)Bca DNA polymerase (Walker and Linn, *Clinical Chemistry* 42:1604-1608 (1996)). Other useful polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)). φ29 DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648-7653 (1993)), adenovirus DNA-binding protein (Zijderveld and van der Vliet, *J. Virology* 68(2):1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)); single-stranded DNA binding proteins (SSB; Rigler and Romano, *J. Biol. Chem.* 270: 8910-8919 (1995)); phage T4 gene 32 protein (Villemain and Giedroc, *Biochemistry* 35:14395-14404 (1996); and calf thymus helicase (Siegel et al., *J. Biol. Chem.* 267:13629-13635 (1992)).

O. KITS

The materials described above can be packaged together in any suitable combination as a kit useful for performing the disclosed method. Kit components in a given kit can be designed and adapted for use together in the disclosed method. For example, disclosed are kits for amplifying genomic DNA, the kit comprising a lysis solution, a stabilization solution, a set of random G-deficient primers, and a DNA polymerase. The components of such a kit are described elsewhere herein. In some forms of the kit, the set of primers can comprise random G-deficient pentamer primers. In some forms of the kit, the DNA polymerase can be φ29 DNA polymerase. In some forms of the kit, the kit can further comprise deoxynucleotide triphosphates. In some forms of the kit, the kit can further comprise one or more detection probes. Detection probes are described elsewhere herein. In some forms of the kit, the detection probes can each comprise a complementary portion, where the complementary portion is complementary to a nucleic acid sequence of interest. In some forms of the kit, the kit can further comprise denaturing solution. In some forms of the kit, the kit can further comprise reaction mix.

Some useful kits can comprise a lysis solution, a stabilization solution, a set of random G-deficient primers, a φ29 DNA polymerase, 1M dithiotheitol, 1× Phosphase-Buffered Saline, pH 7.5, and control DNA template; where the lysis solution comprises 400 mM KOH and 10 mM EDTA, the stabilization solution comprises 800 mM Tris-HCl, pH 4, and the set of primers comprises a reaction mix; where the reaction mix comprises 150 mM Tris-HCl, 200 mM KCl, 40 mM MgCl$_2$, 20 mM (NH$_4$)$_2$SO$_4$, 4 mM deoxynucleotide triphosphates, and 0.2 mM random G-deficient primers.

Any of the components that can be present in a kit that can be used together can be combined in a single component of the kit. Thus, a reaction mix can include, for example, buffers, deoxynucleotide triphosphates and random G-deficient primers. Similarly, components and solutions can be divided into constituent parts or sub-solutions. The kits can be used for any purpose, generally for nucleic acid amplification. In some forms, the kit can be designed to detect nucleic acid sequences of interest in a genome or other nucleic acid sample. In some forms, the kit can be designed to assess a disease, condition or predisposition of an individual based on a nucleic acid sequences of interest.

P. MIXTURES

Also disclosed are mixtures formed by performing, or formed during the course of performing, any form of the disclosed methods. For example, disclosed are mixtures comprising, for example, cells and lysis solution; cell lysate and stabilization solution; stabilized cell lysate and one or more primers; stabilized cell lysate and DNA polymerase; stabilized cell lysate, one or more primers, and DNA polymerase; stabilized cell lysate and replicated strands; stabilized cell lysate, one or more primers, and replicated strands; stabilized cell lysate, DNA polymerase, and replicated strands; stabilized cell lysate, one or more primers, DNA polymerase, and replicated strands; stabilized cell lysate and one or more detection probes; stabilized cell lysate, one or more primers, one or more detection probes, and replicated strands; stabilized cell lysate, DNA polymerase, one or more detection probes, and replicated strands; stabilized cell lysate, one or more primers, DNA polymerase, one or more detection probes, and replicated strands, sample and lysis solution; sample and stabilization solution; stabilized sample and one or more primers; stabilized sample and DNA polymerase; stabilized sample, one or more primers, and DNA polymerase; stabilized sample and replicated strands; stabilized sample, one or more primers, and replicated strands; stabilized sample, DNA polymerase, and replicated strands; stabilized sample, one or more primers, DNA polymerase, and replicated strands; stabilized sample and one or more detection probes; stabilized sample, one or more primers, one or more detection probes, and replicated strands; stabilized sample, DNA polymerase, one or more detection probes, and replicated strands; and stabilized sample, one or more primers, DNA polymerase, one or more detection probes, and replicated strands.

Whenever the method involves mixing or bringing into contact, for example, compositions or components or reagents, performing the method creates a number of different mixtures. For example, if the method includes three mixing steps, after each one of these steps a unique mixture is formed if the steps are performed sequentially. In addition, a mixture is formed at the completion of all of the steps regardless of how the steps were performed. The present disclosure contemplates these mixtures, obtained by the performance of the disclosed method as well as mixtures containing any disclosed reagent, composition, or component, for example, disclosed herein.

Uses

The disclosed methods and compositions are applicable to numerous areas including, but not limited to, analysis of nucleic acids present in cells (for example, analysis of genomic DNA in cells), disease detection, mutation detection, gene discovery, gene mapping (molecular haplotyping), and agricultural research. Particularly useful is whole genome amplification. Other uses include, for example, detection of nucleic acids in cells and on genomic DNA arrays; molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Methods

Disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands.

Also disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands, wherein none of the random G-deficient primers comprises three or more consecutive guanine residues or none of the random G-deficient primers comprises two or more consecutive guanine residues at the 3' end, or wherein none of the random G-deficient primers comprises three or more consecutive guanine residues and none of the random G-deficient primers comprises two or more consecutive guanine residues at the 3' end.

Disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands, wherein at least one of the replicated strands is displaced from the target sequence by strand displacement replication of another replicated strand.

Also disclosed herein are methods of randomly amplifying a target nucleic acid sequence, wherein the target sample is not subjected to denaturing conditions.

Disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands, further comprising labeling the replicated strands.

Also disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands, wherein the target sample is not subjected to heat denaturing conditions, wherein the conditions that promote replication of the target sequence are substantially isothermic, wherein the conditions that promote replication of the target sequence do not involve thermal cycling and/or wherein the conditions that promote replication of the target sequence involve thermal cycling.

Disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein replication of the target sequence results in replicated strands, further, comprising diluting the replicated strands, contacting the diluted replicated strands with a second set of primers and DNA polymerase, and incubating the replicated strands under conditions that promote replication of the target sequence, wherein replication of the target sequence results in additional replicated strands, wherein during replication at least one of the additional replicated strands is displaced from the target sequence by strand displacement replication of another additional replicated strand. In such methods, the primers of the second set of primers can also be random G-deficient primers.

Also disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein nucleic acids in the target sample are not separated from other material in the target sample. The target sample in such methods can be a crude cell lysate. "Other material" refers to any material other than nucleic acids present in a sample. For example, other material can refer to cellular components such as proteins, lipids, sugars or other cellular debris found in a sample other than the nucleic acids present in the same sample.

Also disclosed herein are methods of randomly amplifying a target nucleic acid sequence, the method comprising, bringing into contact a set of primers, DNA polymerase, and a target sample, wherein the primers are random G-deficient primers, and incubating the target sample under conditions that promote replication of the target sequence, wherein nucleic acids in the target sample are not separated from other material in the target sample, wherein replication of the target sequence results in replicated strands, wherein during replication at least one of the replicated strands is displaced from the target sequence by strand displacement replication of another replicated strand.

Also disclosed herein are methods of randomly amplifying messenger RNA, the method comprising, reverse transcribing messenger RNA to produce a first strand cDNA, bringing into contact a set of random G-deficient primers, DNA polymerase, and the first strand cDNA, and incubating under conditions that promote replication of the first strand cDNA, wherein replication of the first strand cDNA results in replicated strands, wherein during replication at least one of the replicated strands is displaced from the first strand cDNA by strand displacement replication of another replicated strand.

Also disclosed herein are methods of randomly amplifying a target nucleic acid sequence, the method comprising, mixing a set of random G-deficient primers with a target sample, to produce a primer-target sample mixture, and incubating the primer-target sample mixture under conditions that promote hybridization between the random G-deficient primers and the target sequence in the primer-target sample mixture, mixing DNA polymerase with the primer-target sample mixture, to produce a polymerase-target sample mixture, and incubating the polymerase-target sample mixture under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity.

Also disclosed herein are methods of randomly amplifying a target nucleic acid sequence, the method comprising, mixing a set of random G-deficient primers with a target sample, to produce a primer-target sample mixture, and incubating the primer-target sample mixture under conditions that promote hybridization between the random G-deficient primers and the target sequence in the primer-target sample mixture, mixing DNA polymerase with the primer-target sample mixture, to produce a polymerase-target sample mixture, and incubating the polymerase-target sample mixture under conditions that promote replication of the target sequence, wherein replication of the target sequence results in replicated strands, wherein during replication at least one of the replicated strands is displaced from the target sequence by strand displacement replication of another replicated strand, wherein the target sequence is a nucleic acid sample of substantial complexity further comprising the step of thermal cycling to allow hybridization between the random G-deficient primers and the replicated strands, and incubating under conditions that promote replication of the target sequence and replicated strands. The conditions that promote replication of the target sequence in such methods can be substantially isothermic, do not involve thermal cycling, or they can involve thermal cycling.

Also disclosed are methods of randomly amplifying a whole genome, the method comprising, bringing into contact a set of random G-deficient primers, DNA polymerase, and a target sample, and incubating the target sample under conditions that promote replication of the target sequence.

Also disclosed are methods of randomly amplifying a whole genome, the method comprising, bringing into contact a set of random G-deficient primers, DNA polymerase, and a target sample, and incubating the target sample under conditions that promote replication of the target sequence, wherein the target sample is not subjected to denaturing conditions Also disclosed are methods of randomly amplifying a whole genome, the method comprising, bringing into contact a set of random G-deficient primers, DNA polymerase, and a target sample, and incubating the target sample under conditions that promote replication of the target sequence, wherein replication of the target sequence results in replicated strands.

For all the methods disclosed herein, following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A preferred form of labeling involves labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

In the disclosed methods amplification can take place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the whole genome strand displacement method.

Genetic analysis must frequently be carried out with DNA derived from biological samples, such as blood, tissue culture cells, buccal swabs, mouthwash, stool, tissues slices, biopsy aspiration, and archeological samples such as bone or mummified tissue. In some cases, the samples are too small to extract a sufficient amount of pure DNA and it is necessary to carry out DNA-based assays directly from the unprocessed sample. Furthermore, it is time consuming to isolate pure DNA, and so the disclosed method, which can amplify the genome directly from biological samples, represents a substantial improvement.

The disclosed method has several distinct advantages over current methodologies. The genome can be amplified directly from whole blood or cultured cells with simple cell lysis techniques such as KOH treatment. PCR and other DNA amplification methods are severely inhibited by cellular contents and so purification of DNA is needed prior to amplification and assay. For example, heme present in lysed blood cells inhibits PCR. In contrast, the disclosed form of whole genome amplification can be carried out on crude lysates with no need to physically separate DNA by miniprep extraction and precipitation procedures, or with column or spin cartridge methods.

Bacteria, fungi, and viruses may all be involved in nosocomial infections. Identification of nosocomial pathogens at the sub-species level requires sophisticated discriminatory techniques. Such techniques utilize traditional as well as molecular methods for typing. Some traditional techniques are antimicrobial susceptibility testing, determination of the ability to utilize biochemical substrates, and serotyping. A major limitation of these techniques is that they take several days to complete, since they require pure bacterial cultures. Because such techniques are long, and the bacteria may even be non-viable in the clinical samples, there is a need to have a quick and reliable method for bacterial species identification.

Some of the DNA-based molecular methods for the identification of bacterial species are macrorestriction analysis (MRA) followed by pulsed-field gel electrophoresis (PFGE), amplified fragment length polymorphism (AFLP) analysis, and arbitrarily primed PCR (AP-PCR) (Tenover et al., J. Clin. Microbiol. 32:407-415 (1994), and Pruckler et al., J. Clin. Microbiol. 33:2872-2875 (1995)). These molecular techniques are labor-intensive and difficult to standardize among different laboratories.

The disclosed method provides a useful alternative method for the identification of bacterial strains by amplification of microbial DNA for analysis. Unlike PCR (Lantz et al., Biotechnol. Annu. Rev. 5:87-130 (2000)), the disclosed method is rapid, non-biased, reproducible, and capable of amplifying large DNA segments from bacterial, viral or fungal genomes.

The disclosed method can be used, for example, to obtain enough DNA from unculturable organisms for sequencing or other studies. Most microorganisms cannot be propagated outside their native environment, and therefore their nucleic acids cannot be sequenced. Many unculturable organisms live under extreme conditions, which makes their genetic complement of interest to investigators. Other microorganisms live in communities that play a vital role in certain ecosystems. Individual organisms or entire communities of organisms can be amplified and sequenced, individually or together.

Recombinant proteins may be purified from a large biomass grown up from bacterial or yeast strains harboring desired expression vectors. A high degree of purity may be desired for the isolated recombinant protein, requiring a sensitive procedure for the detection of trace levels of protein or DNA contaminants. The disclosed method is a DNA amplification reaction that is highly robust even in the presence of low levels of DNA template, and can be used to monitor preparations of recombinant protein for trace amounts of contaminating bacterial or yeast genomic DNA.

Amplification of forensic material for RFLP-based testing is one useful application for the disclosed method.

Also disclosed is a method for amplifying and repairing damaged DNA. This method is useful, for example, for amplifying degraded genomic DNA. The method involves substantially denaturing a damaged DNA sample (generally via exposure to heat and alkaline conditions), removal or reduction of the denaturing conditions (such as by reduction of the pH and temperature of the denatured DNA sample), and replicating the DNA. The damaged DNA is repaired during replication by increasing the average length of the damaged DNA. For example, the average length of DNA fragments can be increase from, for example, 2 kb in the damaged DNA sample to, for example, 10 kb or greater for the replicated DNA. This repair method can result in an overall improvement in amplification of damaged DNA by increasing the average length of the product, increasing the quality of the amplification products by 3-fold (by, for example, increasing the marker representation in the sample), and improving the genotyping of amplified products by lowering the frequency of allelic dropout; all compared to the results when amplifying damaged DNA by other methods. The removal of denaturing conditions can allow denatured strands of damaged DNA to hybridize to other denatured damaged DNA. The replication can be multiple displacement amplification. Substantial denaturation and transient denaturation of the DNA samples generally is carried out such that the DNA is not further damaged. This method can generally be combined or used with any of the disclosed amplification methods.

It has been discovered that it is unnecessary to have prior knowledge of whether or not a sample contains amplifiable nucleic acids. Some forms of the disclosed methods can be employed to test whether or not a sample suspected of containing nucleic acids actually does contain nucleic acids. Production of amplified DNA from such samples using the disclosed method is evidence that the sample contained nucleic acids. More generally, practice of the disclosed methods does not require any knowledge of any nucleic acid sequence in a sample. Thus, the disclosed methods can be used to amplify nucleic acids from any source, regardless of a lack of specific sequence information. This is in contrast to other amplification methods, such as PCR, where it is necessary to have prior information of at least a portion of the nucleic acid sequences believed to be present in the sample in order to perform the amplification. In this instance, the PCR amplification reaction will fail if the nucleic acids present in the sample are different from the expected sample nucleic acids. If a sample contains a mixture of nucleic acids, then nucleic acids of the appropriate type alone will be amplified in a PCR reaction, but not the other types of nucleic acids. In contrast, the disclosed methods provide for amplification of most or all of the nucleic acids present in the sample. The disclosed methods are equally adaptable to using samples that conventionally are not expected or believed to contain nucleic acids. For instance, serum or plasma from humans or other higher animals were believed to not contain free host nucleic acids. However, it was discovered that the disclosed methods could amplify nucleic acids present in such samples.

Also disclosed are methods of amplifying a target nucleic acid sequence in a continuous, isothermal reaction. Also disclosed are methods of amplifying an entire genome or other highly complex nucleic acid sample in a continuous, isothermal reaction. Also disclosed are methods of amplifying a target nucleic acid sequence where multiple copies of the target nucleic acid sequence are produced in a single amplification cycle. Also disclosed are methods of amplifying a concatenated DNA in a continuous, isothermal reaction. Also disclosed are kits for amplifying a target nucleic acid sequence in a continuous, isothermal reaction. Also disclosed are kits for amplifying an entire genome or other highly complex nucleic acid sample in a continuous, isothermal reaction.

In the disclosed methods, a genomic sample can be prepared by exposing the sample to alkaline conditions to denature the nucleic acids in the sample; reducing the pH of the sample to make the pH of the sample compatible with DNA replication; and incubating the sample under conditions that promote replication of the genome.

Also in the disclosed methods, the nucleic acid targets can be prepared in a single-stranded form during sample preparation procedures. For example, nucleic acid targets can be prepared using sequence-specific hybrid capture sample preparations. Single-stranded targets can be used in the disclosed methods for example to detect specific pathogens such as human pappiloma virus (HPV).

Also disclosed herein are methods of randomly amplifying a target nucleic acid sequence, wherein a sample that may comprise nucleic acids is exposed to alkaline conditions, where the alkaline conditions promote lysis of cells that may be present in the sample (although the sample need not contain cells), reducing the pH of all or a portion of the sample to form a stabilized sample, and incubating an amplification mixture under conditions that promote replication of the nucleic acids from the sample, where the amplification mixture comprises all or a portion of the stabilized sample. Replication of the nucleic acids results in replicated strands, where during replication at least one of the replicated strands is displaced from nucleic acids in the sample by strand displacement replication of another replicated strand, where the replicated strands have low amplification bias. The concentration of nucleic acids in the amplification mixture can be chosen to favor hybridization of primers over reassociation of the nucleic acids. Further, the amount of nucleic acids in the amplification mixture can be at or above a threshold that can result in low amplification bias in the replicated strands.

As described elsewhere herein, the disclosed methods can be performed on any desired samples. For example, the disclosed methods can be performed using samples that contain or are suspected of containing nucleic acids. Some forms of the disclosed methods do not require knowledge of any sequence present in a sample in order to amplify nucleic acids in the sample. Accordingly, some forms of the disclosed methods can be used to determine if a sample contains nucleic acids. If amplification products are produced when the method is performed, the sample contains nucleic acids. The disclosed methods can be performed on cells and on nucleic acid samples, including crude nucleic acid samples, partially purified nucleic acid sample, and purified nucleic acid samples. Exposing any cell or nucleic acid sample to alkaline conditions and then reducing the pH of the sample can produce a stabilized sample suitable for amplification or replication.

The disclosed methods can also comprise strand displacement replication of the nucleic acid sequences by multiple primers. The method can be used to amplify one or more specific sequences (multiple strand displacement amplification), an entire genome or other DNA of high complexity (whole genome strand displacement amplification), or concatenated DNA (multiple strand displacement amplification of concatenated DNA). The disclosed methods can involve hybridization of primers to a target nucleic acid sequence and replication of the target sequence primed by the hybridized primers such that replication of the target sequence results in replicated strands complementary to the target sequence. During replication, the growing replicated strands can displace other replicated strands from the target sequence (or from another replicated strand) via strand displacement replication. As used herein, a replicated strand is a nucleic acid strand resulting from elongation of a primer hybridized to a target sequence or to another replicated strand. Strand displacement replication refers to DNA replication where a growing end of a replicated strand encounters and displaces another strand from the template strand (or from another replicated strand). Displacement of replicated strands by other replicated strands allows multiple copies of a target sequence to be made in a single, isothermic reaction.

The disclosed methods can accurately and evenly amplify the various sequences in highly complex nucleic acid samples. This result can be quantified by references to, for example, percent representation, sequence representation, sequence representation bias, percent sequence representation, locus representation, locus representation bias, percent locus representation, and/or amplification bias. For example, the replicated nucleic acid molecules produced in the disclosed method can have a sequence representation or sequence representation bias of at least 50% for at least 10 different target sequences. The amplification bias can be less than 10% for at least 10 different target sequences.

Nucleic acids for amplification can be obtained from cellular samples. This generally requires disruption of the cell (to make the nucleic acid accessible) and purification of the nucleic acids prior to amplification. It also generally requires the inactivation of protein factors such as nucleases that could degrade the DNA, or of factors such as histones that could bind to DNA strands and impede their use as a template for DNA synthesis by a polymerase. There are a variety of techniques used to break open cells, such as sonication, enzymatic digestion of cell walls, heating, and exposure to lytic conditions. Lytic conditions typically involve use of non-physiological pH and/or solvents. Many lytic techniques can result in damage to nucleic acids in cells, including, for example, breakage of genomic DNA. In particular, use of heating to lyse cells can damage genomic DNA and reduce the amount and quality of amplification products of genomic DNA. It has been discovered that alkaline lysis can cause less damage to genomic DNA and can thus result in higher quality amplification results. Alkaline lysis also inactivates protein factors such as nucleases, histones, or other factors that could impede the amplification of DNA within the sample. In addition, it is a useful property of alkaline lysis that reducing the pH does not reactivate the protein factors, but that such protein factors remain inactivated when the pH of the solution is brought back within a neutral range. Lysis and Stabilization solutions that can be used in the disclose methods are described in U.S. Pat. Nos. 6,977,148; 6,617,137; 7,074,600; 7,297,485; 6,124,120; 6,280,949; and 6,642,034, which are hereby incorporated by reference in their entirety for their teaching the same.

The concentration of nucleic acids in an amplification mixture can favor hybridization of primers over reassociation of the nucleic acids, which serves to improve the quality of the amplification products (by, for example, providing a lower amplification bias). The concentration at or below which low amplification bias can be achieved can be determined for different samples and for different amplification techniques using methods described herein. The concentration of nucleic acids in the amplification mixture can be, for example, 300 ng/µl or less, 200 ng/µl or less, 150 ng/µl or less, 100 ng/µl or less, 95 ng/µl or less, 90 ng/µl or less, 85 ng/µl or less, 80 ng/µl or less, 75 ng/µl or less, 70 ng/µl or less, 65 ng/µl or less, 60 ng/µl or less, 55 ng/µl or less, 50 ng/µl or less, 45 ng/µl or less, 40 ng/µl or less, 35 ng/µl or less, 30 ng/µl or less, 25 ng/µl or less, 20 ng/µl or less, 15 ng/µl or less, 10 ng/µl or less, 9 ng/µl or less, 8 ng/µl or less, 7 ng/µl or less, 6 ng/µl or less, 5 ng/µl or less, 4 ng/µl or less, 3 ng/µl or less, 2 ng/µl or less, 1 ng/µl or less, 0.8 ng/µl or less, 0.6 ng/µl or less, 0.5 ng/µl or less, 0.4 ng/µl or less, 0.3 ng/µl or less, 0.2 ng/µl or less, or 0.1 ng/µl or less.

The methods disclosed herein can also be used to amplify nucleic acids in lower concentrations. For example, the amount of nucleic acids in an amplification mixture can be as low as 10 copies of the target (e.g. 0.1 fentograms). The concentration of nucleic acids in the amplification mixture can be, for example, 300 pg/µl or less, 200 pg/µl or less, 150 pg/µl or less, 100 pg/µl or less, 95 pg/µl or less, 90 pg/µl or less, 85 pg/µl or less, 80 pg/µl or less, 75 pg/µl or less, 70 pg/µl or less, 65 pg/µl or less, 60 pg/µl or less, 55 pg/µl or less, 50 pg/µl or less, 45 pg/µl or less, 40 pg/µl or less, 35 pg/µl or less, 30 pg/µl or less, 25 pg/µl or less, 20 pg/µl or less, 15 pg/µl or less, 10 pg/µl or less, 9 pg/µl or less, 8 pg/µl or less, 7 pg/µl or less, 6 pg/µl or less, 5 pg/µl or less, 4 pg/µl or less, 3 pg/µl or less, 2 pg/µl or less, 1 pg/µl or less, 0.8 pg/µl or less, 0.6 pg/µl or less, 0.5 pg/µl or less, 0.4 pg/µl or less, 0.3 pg/µl or less, 0.2 pg/µl or less, or 0.1 pg/µl or less.

The concentration of nucleic acids in the amplification mixture can also be, for example, 300 fg/µl or less, 200 fg/µl or less, 150 fg/µl or less, 100 fg/µl or less, 95 fg/µl or less, 90 fg/µl or less, 85 fg/µl or less, 80 fg/µl or less, 75 fg/µl or less, 70 fg/µl or less, 65 fg/µl or less, 60 fg/µl or less, 55 fg/µl or less, 50 fg/µl or less, 45 fg/µl or less, 40 fg/µl or less, 35 fg/µl or less, 30 fg/µl or less, 25 fg/µl or less, 20 fg/µl or less, 15 fg/µl or less, 10 fg/µl or less, 9 fg/µl or less, 8 fg/µl or less, 7 fg/µl or less, 6 fg/µl or less, 5 fg/µl or less, 4 fg/µl or less, 3 fg/µl or less, 2 fg/µl or less, 1 fg/µl or less, 0.8 fg/µl or less, 0.6 fg/µl or less, 0.5 fg/µl or less, 0.4 fg/µl or less, 0.3 fg/µl or less, 0.2 fg/µl or less, or 0.1 fg/µl or less.

The amount of nucleic acids in an amplification mixture can be at or above a threshold amount, which serves to improve the quality of the amplification products (by, for example, providing a lower amplification bias). The amount at or above which low amplification bias can be achieved can be determined for different samples and for different amplification techniques using methods described herein. The amount of nucleic acids in the amplification mixture can be, for example, at least 50 ng, at least 60 ng, at least 70 ng, at least 80 ng, at least 90 ng, at least 100 ng, at least 110 ng, at least 120 ng, at least 130 ng, at least 140 ng, at least 150 ng, at least 160 ng, at least 170 ng, at least 180 ng, at least 190 ng, at least 200 ng, at least 220 ng, at least 240 ng, at least 260 ng, at least 280 ng, at least 300 ng, at least 325 ng, at least 350 ng, at least 375 ng, at least 400 ng, at least 450 ng, or at least 500 ng.

In some forms of the disclosed methods, the random G-deficient primers can be pentamer primers. It was discovered that such short, 5 nucleotide random G-deficient primers can still prime multiple strand displacement replication efficiently. Such short random G-deficient primers are easier to produce as a complete set of primers of random G-deficient sequence (random G-deficient primers) than longer primers at least because there are fewer to make. In another form of the method, the random G-deficient primers can each contain at least one modified nucleotide such that the primers are nuclease resistant. In another form of the method, the random G-deficient primers can each contain at least one modified nucleotide such that the melting temperature of the primer is altered relative to a random G-deficient primers of the same sequence without the modified nucleotide(s). In another form of the method, the DNA polymerase can be φ29 DNA polymerase. It was discovered that φ29 DNA polymerase produces greater amplification in multiple displacement amplification. The combination of two or more of the above features also yields improved results in multiple displacement amplification. In a preferred embodiment, for example, the target sample is not subjected to denaturing conditions, the random G-deficient primers are pentamer primers and contain modified nucleotides such that the random G-deficient primers are nuclease resistant, and the DNA polymerase is φ29 DNA polymerase. The above features are especially useful in whole genome strand displacement amplification (WGSDA).

In other forms of the disclosed methods, the method includes labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

Some forms of the disclosed methods provide amplified DNA of higher quality relative to previous methods due to the lack of a heat denaturation treatment of the DNA that is the target for amplification. Thus, the template DNA does not undergo the strand breakage events caused by heat treatment and the amplification that is accomplished by a single DNA polymerase extends farther along template strands of increased length.

In some forms of the disclosed methods, a small amount of purified double-strand human genomic DNA (1 ng, for example) can be mixed with exonuclease-resistant random G-deficient primers and φ29 DNA polymerase under conditions that favor DNA synthesis. For example, the mixture can simply be incubated at 30° C. and multiple displacement amplification will take place. Thus, any single-stranded or duplex DNA may be used, without any additional treatment, making the disclosed method a simple, one-step procedure. Since so little DNA template is required, a major advantage of the disclosed method is that DNA template may be taken from preparations that contain levels of contaminants that would inhibit other DNA amplification procedures such as PCR. For MDA the sample may be diluted so that the contaminants fall below the concentration at which they would interfere with the reaction. The disclosed methods can be performed (and the above advantages achieved) using any type of sample, including, for example, bodily fluids such as urine, semen, lymphatic fluid, cerebrospinal fluid, and amniotic fluid.

The need for only small amounts of DNA template in the disclosed methods means that the methods are useful for DNA amplification from very small samples. In particular, the disclosed methods can be used to amplify DNA from a single cell. The ability to obtain analyzable amounts of nucleic acid from a single cell (or similarly small sample) has many applications in preparative, analytical, and diagnostic procedures such as prenatal diagnostics. Other examples of biological samples containing only small amounts of DNA for which amplification by the disclosed method would be useful are material excised from tumors or other archived medical samples, needle aspiration biopsies, clinical samples arising from infections, such as nosocomial infections, forensic samples, or museum specimens of extinct species.

More broadly, the disclosed methods are useful for applications in which the amounts of DNA needed are greater than the supply. For example, procedures that analyze DNA by chip hybridization techniques are limited by the amounts of DNA that can be purified from typically sized blood samples. As a result many chip hybridization procedures utilize PCR to generate a sufficient supply of material for the high-throughput procedures. The disclosed methods present a useful technique for the generation of plentiful amounts of amplified DNA that faithfully reproduces the locus representation frequencies of the starting material.

It has been discovered that it is unnecessary to have prior knowledge of whether or not a sample contains amplifiable nucleic acids. Some forms of the disclosed methods can be employed to test whether or not a sample suspected of containing nucleic acids actually does contain nucleic acids. Production of amplified DNA from such samples using the disclosed method is evidence that the sample contained nucleic acids. More generally, practice of the disclosed methods does not require any knowledge of any nucleic acid sequence in a sample. Thus, the disclosed methods can be used to amplify nucleic acids from any source, regardless of a lack of specific sequence information. This is in contrast to other amplification methods, such as PCR, where it is necessary to have prior information of at least a portion of the nucleic acid sequences believed to be present in the sample in order to perform the amplification. In this instance, the PCR amplification reaction will fail if the nucleic acids present in the sample are different from the expected sample nucleic acids. If a sample contains a mixture of nucleic acids, then nucleic acids of the appropriate type alone will be amplified in a PCR reaction, but not the other types of nucleic acids. In contrast, the disclosed methods provide for amplification of most or all of the nucleic acids present in the sample. The disclosed methods are equally adaptable to using samples that conventionally are not expected or believed to contain nucleic acids. For instance, serum or plasma from humans or other higher animals were believed to not contain free host nucleic acids. However, it was discovered that the disclosed methods could amplify nucleic acids present in such samples.

The disclosed methods, either in whole or in part, can be performed in or on solid supports or in or on reaction chambers. For example, the disclosed replication, incubation and amplification steps can be performed with the amplification mixture in or on solid supports or in or on reaction chambers. For example, the disclosed replication, incubation and amplification steps can be performed with the amplification mixture on solid supports having reaction chambers. A reaction chamber is any structure in which a separate amplification reaction can be performed. Useful reaction chambers include tubes, test tubes, eppendorf tubes, vessels, micro vessels, plates, wells, wells of micro well plates, wells of microtitre plates, chambers, micro fluidics chambers, micro machined chambers, sealed chambers, holes, depressions, dimples, dishes, surfaces, membranes, microarrays, fibers, glass fibers, optical fibers, woven fibers, films, beads, bottles, chips, compact disks, shaped polymers, particles, microparticles or other structures that can support separate reactions. Reaction chambers can be made from any suitable material. Such materials include acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid supports preferably comprise arrays of reaction chambers. In connection with reaction chambers, a separate reaction refers to a reaction where substantially no cross contamination of reactants or products will occur between different reaction chambers. Substantially no cross contamination refers to a level of contamination of reactants or products below a level that would be detected in the particular reaction or assay involved. For example, if nucleic acid contamination from another reaction chamber would not be detected in a given reaction chamber in a given assay (even though it may be present), there is no substantial cross contamination of the nucleic acid. It is understood, therefore, that reaction chambers can comprise, for example, locations on a planar surface, such as spots, so long as the reactions performed at the locations remain separate and are not subject to mixing.

A. Whole Genome Strand Displacement Amplification

In one form of the method, referred to as whole genome strand displacement amplification (WGSDA), a set of random, partially random, degenerate, or a random G-deficient primers can be used to randomly prime a sample of genomic nucleic acid (or another sample of nucleic acid of high complexity). By choosing a sufficiently large set of primers of random, partially random, degenerate, or random G-deficient sequence, the primers in the set will be collectively, and randomly, complementary to nucleic acid sequences distributed throughout nucleic acid in the sample. Amplification proceeds by replication with a processive polymerase initiated at each primer and continuing until spontaneous termination. A key feature of this method is the displacement of intervening primers during replication by the polymerase. In this way, multiple overlapping copies of the entire genome can be synthesized in a short time.

Whole genome strand displacement amplification can be performed by (a) mixing a set of random, partially random, degenerate, or random G-deficient primers primers with a genomic sample (or other nucleic acid sample of high complexity), to produce a primer-target sample mixture, and incubating the primer-target sample mixture under conditions that promote hybridization between the primers and the genomic DNA in the primer-target sample mixture, and (b) mixing DNA polymerase with the primer-target sample mixture, to produce a polymerase-target sample mixture, and incubating the polymerase-target sample mixture under conditions that promote replication of the genomic DNA. Strand displacement replication can be accomplished by using a strand displacing DNA polymerase or a DNA polymerase in combination with a compatible strand displacement factor.

The method has advantages over the polymerase chain reaction since it can be carried out under isothermal conditions. Other advantages of whole genome strand displacement amplification include a higher level of amplification than whole genome PCR, amplification is less sequence-dependent than PCR, a lack of re-annealing artifacts or gene shuffling artifacts as can occur with PCR (since there are no cycles of denaturation and re-annealing), and a lower amplification bias than PCR-based genome amplification (bias of 3-fold for WGSDA versus 20- to 60-fold for PCR-based genome amplification).

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction.

The set of primers used for WGSDA can be used at concentrations that allow the primers to hybridize at desired intervals within the nucleic acid sample. For example, by using a set of primers at a concentration that allows them to hybridize, on average, every 4000 to 8000 bases, DNA replication initiated at these sites will extend to and displace strands being replicated from adjacent sites. It should be noted that the primers are not expected to hybridize to the target sequence at regular intervals. Rather, the average interval will be a general function of primer concentration.

As in multiple strand displacement amplification, displacement of an adjacent strand makes it available for hybridization to another primer and subsequent initiation of another round of replication. The interval at which primers in the set of primers hybridize to the target sequence determines the level of amplification. For example, if the average interval is short, adjacent strands will be displaced quickly and frequently. If the average interval is long, adjacent strands will be displaced only after long runs of replication.

In the disclosed method, the DNA polymerase catalyzes primer extension and strand displacement in a processive strand displacement polymerization reaction that proceeds as long as desired. Examples of strand displacing DNA polymerases include, but are not limited to, bacteriophage φ29 DNA polymerase (U.S. Pat. Nos. 5,198,543 and 5,001,050 to Blanco et al.), large fragment Bst DNA polymerase (Exo(−) Bst), exo(−)Bca DNA polymerase, and Sequenase.

During strand displacement replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al., *Proc. Natl. Acad. Sci. USA* 78:6633 (1981)).

Genome amplification using PCR, and uses for the amplified DNA, is described in Zhang et al., *Proc. Natl. Acad. Sci. USA* 89:5847-5851 (1992), Telenius et al., *Genomics* 13:718-725 (1992), Cheung et al., *Proc. Natl. Acad. Sci. USA* 93:14676-14679 (1996), and Kukasjaarvi et al., *Genes, Chromosomes and Cancer* 18:94-101 (1997). The uses of the amplified DNA described in these publications are also generally applicable to DNA amplified using the disclosed methods. Whole Genome Strand Displacement Amplification, unlike PCR-based whole genome amplification, is suitable for haplotype analysis since WGSDA yields longer fragments than PCR-based whole genome amplification. PCR-based whole genome amplification is also less suitable for haplotype analysis since each cycle in PCR creates an opportunity for priming events that result in the association of distant sequences (in the genome) to be put together in the same fragment.

B. Multiple Strand Displacement Amplification

Multiple strand displacement amplification can be performed by (a) mixing a set of primers with a target sample, to produce a primer-target sample mixture, and incubating the primer-target sample mixture under conditions that promote hybridization between the primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence. Primers for use in MSDA can be random G-deficient primers. For example, disclosed is a method of amplifying a nucleic acid comprising (a) mixing a set of random G-deficient primers with a target sample, to produce a primer-target sample mixture, and incubating the primer-target sample mixture under conditions that promote hybridization between the primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence Strand displacement replication can be accomplished by using a strand displacing DNA polymerase or a DNA polymerase in combination with a compatible strand displacement factor. The disclosed method has advantages over the polymerase chain reaction since it can be carried out under isothermal conditions. No thermal cycling is needed because the polymerase at the head of an elongating strand (or a compatible strand-displacement factor) will displace, and thereby make available for hybridization, the strand ahead of it. Other advantages of multiple strand displacement amplification include the ability to amplify very long nucleic acid segments (on the order of 50 kilobases) and rapid amplification of shorter segments (10 kilobases or less). Long nucleic acid segments can be amplified in the disclosed method since there is no cycling which could interrupt continuous synthesis or allow the formation of artifacts due to rehybridization of replicated strands.

C. Multiple Strand Displacement Amplification of Concatenated DNA

In another form of the method, referred to as multiple strand displacement amplification of concatenated DNA (MSDA-CD), concatenated DNA is amplified. A preferred form of concatenated DNA is concatenated cDNA. Concatenated DNA can be amplified using a random, partially random, or random G-deficient set of primers, as in WGSDA, or using specific primers complementary to specific hybridization targets in the concatenated DNA. MSDA-CD is preferred for amplification of a complex mixture or sample of relatively short nucleic acid samples (that is, fragments generally in the range of 100 to 6,000 nucleotides). Messenger RNA is the most important example of such a complex mixture. MSDA-CD provides a means for amplifying all cDNAs in a cell is equal fashion. Because the concatenated cDNA can be amplified up to 5,000-fold, MSDA-CD will permit RNA profiling analysis based on just a few cells. To perform MSDA-CD, DNA must first be subjected to a concatenation step. If an RNA sample (such as mRNA) is to be amplified, the RNA is first converted to a double-stranded cDNA using standard methods. The cDNA, or any other set of DNA fragments to be amplified, is then converted into a DNA concatenate, preferably with incorporation of linkers.

D. Multiple Strand Displacement Amplification of Damaged DNA

Other forms of the disclosed method can involve amplification and repair of damaged DNA. Amplification of damaged DNA can be both difficult and provide unreliable results. For example, amplification of degraded or fragmented DNA will produce truncated products and can result in allele dropout. Preparation of genomic DNA samples in particular can result in damage to the genomic DNA (for example, degradation and fragmentation). Damaged DNA and damaged DNA samples can be amplified and repaired in the disclosed method of amplifying damage DNA. The method generally works by hybridizing the ends of some DNA molecules in a damaged DNA sample to complementary sequences in the sample. Because the DNA molecules providing the newly associated ends will have damage at different locations, priming from the annealed ends can result in replication of more complete fragments and can mediate repair of the damaged DNA (in the form of less damaged or undamaged replicated strands). Replication of the undamaged replicated strands by continued multiple displacement amplification produces less damaged or undamaged amplified nucleic acids.

The method generally involves substantially denaturing a damaged DNA sample (generally via exposure to heat and alkaline conditions), removal or reduction of the denaturing conditions (such as by reduction of the pH and temperature of the denatured DNA sample), and replicating the DNA. The damaged DNA is repaired during replication and the average length of DNA fragments is increased. For example, the average length of DNA fragments can be increase from, for example, 2 kb in the damaged DNA sample to, for example, 10 kb or greater for the replicated DNA. The amplified and repaired DNA is in better condition for analysis and testing than the damaged DNA sample. For example, this technique can provide consistent improvements in allele representation from damaged DNA samples. This repair method can result in an overall improvement in amplification of damaged DNA by increasing the average length of the product, increasing the quality of the amplification products by 3-fold (by, for example, increasing the marker representation in the sample), and improving the genotyping of amplified products by lowering the frequency of allelic dropout; all compared to the results when amplifying damaged DNA by other methods. The replication can be multiple displacement amplification. Denaturation of the DNA sample generally is carried out such that the DNA is not further damaged. This method can generally be combined or used with any of the disclosed amplification methods.

In some embodiments, the method of amplifying damaged DNA can involve exposing a damaged DNA sample to conditions that promote substantial denaturation of damaged DNA in the damaged DNA sample, thereby forming a denatured damaged DNA sample; altering the conditions to conditions that do not promote substantial denaturation of damaged DNA in the damaged DNA sample to form a stabilized denatured damaged DNA sample; and incubating the annealed damaged DNA under conditions that promote replication of the damaged DNA. The annealed ends of the damaged DNA prime replication and replication of the damaged DNA results in repair of the replicated strands. The conditions that promote substantial denaturation of damaged DNA in the damaged DNA sample can be, for example, raising the pH of the damaged DNA sample and heating the damaged DNA sample. The altering conditions can be, for example, reducing the pH of the denatured damaged DNA sample and cooling the damaged DNA sample. Raising the pH can be accomplished by exposing the damaged DNA sample to alkaline conditions. The altering conditions generally can be conditions that promote annealing of the ends of the transiently denatured damaged DNA to the substantially denatured damaged DNA. The damaged DNA sample, the denatured damaged DNA sample, or both can also be exposed to ionic conditions by, for example, mixing the damaged DNA sample or denatured damaged DNA sample with an ionic solution or including salt(s) or other ions in the denaturing solution, the stabilization solution, or both.

In the method, the damaged DNA sample can be exposed to conditions that promote substantial denaturation by, for example, mixing the damaged DNA sample with a denaturing solution and by heating the damaged DNA sample to a temperature and for a length of time that substantially denatures the damaged DNA in the damaged DNA sample. The pH of the denatured damaged DNA sample can be reduced, for example, by mixing the denatured damaged DNA sample with a stabilization solution. The damaged DNA samples can be, for example, degraded DNA fragments of genomic DNA. Replication and repair of the damaged DNA can be accomplished by incubating the damaged DNA in the presence of a DNA polymerase, such as $\phi_{29}$ DNA polymerase.

The damaged DNA sample can generally be slowly cooled in order to achieve the required annealing. The rate of cooling of the damaged DNA sample can also described in terms of the percent drop in temperature. The damaged DNA sample, the denatured damaged DNA sample, or both can also be exposed to ionic conditions by, for example, mixing the damaged DNA sample or denatured damaged DNA sample with an ionic solution or including salt(s) or other ions in the denaturing solution, the stabilization solution, or both. As used herein, ionic conditions refers to a state of increased ionic strength. Thus, exposure to ionic conditions refers to exposure to a higher ionic strength than existed in the sample or solution before exposure. This will be the result when, for example, a buffer or salt is added. A solution used to make such an addition can be referred to as an ionic solution. The ionic solution can be a salt solution and can comprise one or more salts or other ions. Any suitable salt or ion can be used. The salt can be, for example, Tris-HCl, Tris-EDTA, sodium chloride, potassium chloride, magnesium chloride, sodium acetate, potassium acetate, magnesium acetate, or a combination. The Tris-HCl can be, for example, from pH 7.0 to 8.0. The salt can be Tris-EDTA. The ionic solution can be diluted, for example, 2 to 5 fold when mixed with the damaged DNA sample. The ionic solution can be mixed with the denatured damaged DNA sample prior to or during altering of the conditions.

Ionic conditions and the composition of ionic solutions generally can be can be specified by specifying a concentration of a buffer, salt, or other ion-forming compound. A combination of compounds can be used in an ionic solution or to create ionic conditions. The disclosed method of repairing and amplifying DNA can result in an increase in the average length of DNA fragment in a DNA sample. This increase can be referred to in any suitable terms. For example, the increase in average fragment length can be referred to by the average fragment length of the replicated DNA fragments, the increase in average fragment length from the average fragment length of the damaged DNA sample, and the percent increase in average fragment length.

The disclosed method of amplifying damaged DNA can be combined with the disclosed amplification of cell lysates and samples. Thus, for example, the damaged DNA samples can be a cell lysate or sample, where the cell lysate or sample is produced by exposing cells or the sample to alkaline conditions. Some forms of the method can include exposing cells to alkaline conditions to form a cell lysate; exposing the cell lysate to conditions that promote substantial denaturation of damaged DNA in the cell lysate; reducing the pH of the cell lysate to form a stabilized cell lysate; cooling the stabilized cell lysate under conditions that promote annealing of the ends of the denatured damaged DNA; and incubating the stabilized cell lysate under conditions that promote replication of the damaged DNA. During replication, the annealed ends of the damaged DNA prime replication and replication of the damaged DNA results in repair of the replicated strands and an increase in the average length of DNA fragment. The cell lysate or sample can be a whole genome. Replication of the genome results in replicated strands, where during replication at least one of the replicated strands is displaced from the genome by strand displacement replication of another replicated strand.

In another form, the method works by hybridizing the ends of some DNA molecules in a sample to complementary sequences in a damaged DNA sample. Generally, the damaged DNA sample and the DNA sample providing the annealed ends or from the same source or even the same sample. Because the DNA molecules providing the newly associated ends and damaged DNA molecules will have damage at different locations, priming from the annealed ends can result in replication of more complete fragments and can mediate repair of the damaged DNA (in the form of less damaged or undamaged replicated strands). Replication of the undamaged replicated strands by continued multiple displacement amplification produces less damaged or undamaged amplified nucleic acids.

The method generally involves substantially denaturing a damaged DNA sample (generally via exposure to heat and alkaline conditions), reduction of the pH of the denatured DNA sample, mixing the denatured DNA sample with an undenatured DNA sample from the same source such that the ends of DNA in the undenatured DNA sample is transiently denatured, slowly, cooling the mixture of DNA samples to allow the transiently denatured ends to anneal to the denatured DNA, and replicating the annealed DNA. The damaged DNA is repaired during replication. The replication can be multiple displacement amplification. Substantial denaturation and transient denaturation of the DNA samples generally is carried out such that the DNA is not further damaged. This method can generally be combined or used with any of the disclosed amplification methods.

In some embodiments, the method of amplifying damaged DNA can involve exposing a first damaged DNA sample to conditions that promote substantial denaturation of damaged DNA in the first damaged DNA sample, thereby forming a denatured damaged DNA sample; reducing the pH of the denatured damaged DNA sample to form a stabilized denatured damaged DNA sample; mixing a second damaged DNA sample with the stabilized denatured damaged DNA sample under conditions that promote transient denaturation of the ends of damaged DNA in the second sample and that maintain substantial denaturation of the damaged DNA in the stabilized denatured damaged DNA sample, thereby forming a damaged DNA mixture; cooling the damaged DNA mixture under conditions that promote annealing of the ends of the transiently denatured damaged DNA to the substantially denatured damaged DNA; and incubating the annealed damaged DNA under conditions that promote replication of the damaged DNA. The annealed ends of the damaged DNA prime replication and replication of the damaged DNA results in repair of the replicated strands.

In the method, the first damaged DNA sample can be exposed to conditions that promote substantial denaturation by, for example, mixing the first damaged DNA sample with a denaturing solution and by heating the first damaged DNA sample to a temperature and for a length of time that substantially denatures the damaged DNA in the first damaged DNA sample. The temperature can be, for example, about 25° C. to about 50° C. and the length of time can be, for example, about 5 minutes or more. The pH of the denatured damaged DNA sample can be reduced, for example, by mixing the denatured damaged DNA sample with a stabilization solution. The damaged DNA samples can be, for example, degraded DNA fragments of genomic DNA. The first and second damaged DNA samples can be from the same source, and in particular can be a portion of the same damaged DNA sample. The second damaged DNA sample can be mixed with the stabilized denatured damaged DNA sample at a temperature and for a length of time that transiently denatures the damaged DNA in the second damaged DNA sample. For example, the temperature can be about 70° C. or less and the length of time can be about 30 seconds or less. The desired effect can also be achieved by maintaining the mixture at the temperature to which the first damaged DNA sample is exposed for denaturation. Replication and repair of the damaged DNA can be accomplished by incubating the annealed damaged DNA in the presence of a DNA polymerase, such as φ29 DNA polymerase.

E. Analysis of Amplification Products

Clinical and health science studies require ready access to large quantities of genomic DNA to serve as inputs for multiparametric assays of polymorphic sites in DNA, whose combined results provide valuable prognostic and diagnostic information. However, these studies are hampered by severe lack of adequate supply of DNA, as most biopsy methods yield only minute quantities of tissue or cells. Sample preparative steps further reduce the amounts recovered from these cells due to loss during cell fractionation, thereby limiting the number of chromosomal loci that can be examined per sample using the isolated genomic DNA as input. Methods of the present invention seek to overcome these shortages by providing adequate and renewable supply of DNA for the multiparametric analyses.

Analysis of loss of heterozygosity (LOH), a relatively common type of genetic alteration found throughout the genome in most solid neoplasms, is frequently employed in cancer diagnosis. While a number of familial cancer genes with high-penetrance mutations are readily identified, success in determining clinical outcomes by LOH analysis to evaluate risk of sporadic cancer development is predicated also on contributions from low-penetrance genetic variants or polymorphisms. Such multiparametric assays require simultaneous analysis of a large number of candidate and other genetic loci from each sample for effective determination and statistical evaluation of disease progression and staging that are presently beyond the scope of measurements using native DNA prepared from the clinical sample. Amplification of genomic DNA present in these samples is a useful adjunct for providing the necessary amounts of DNA required for the multiparametric analyses. The disclosed methods can provide high quality nucleic acids that provides sufficient material for analyses such as LOH analyses.

The progressive loss of form and structure of DNA in cancer cells culminates in dozens of different genes becoming aberrant in nucleotide sequence or copy number, with hundreds or thousands of genes being differentially expressed in diseased cells compared to normal or premalignant cells. Elucidating the temporal and spatial attributes of the complex somatic genetic events delineating emerging cancer cells will aid the search for the more elusive germline variants that confer increased susceptibility. The disclosed methods can provide sufficient amounts of nucleic acids amplified from sample sources to analyze these extensive changes in the genome. This can allow increased throughput of such measurements and efficient utilization of DNA recovered from these samples.

Some forms of the disclosed methods provide accurate and reproducible replication of sample DNA, so as to generate minimal, if any, changes in nucleotide sequence distributions of replicated DNA strands from that of the input DNA. Many prior nucleic acid amplification methods introduce at least some significant degree of artifactual variation in sequence of the amplified DNA leading to bias in the representation of different sequences in the amplified nucleic acids relative to representation of those sequences in the starting nucleic acids. Such bias can be referred to as sequence bias or allele bias.

Some forms of the disclosed methods provide for minimal differences in allele ratios between input nucleic acids and amplification products (which is allele bias—a form of amplification bias). Allele ratio can be defined as the peak height (that is, amount detected) of the smaller allele divided by that of the larger allele (Paulson et al, 1999; herein incorporated by reference). Typically, allele ratios of a sample set of selected genetic loci are measured by performing genotyping assays of replicated or input DNA using a standard genotyping assay. Genotyping assays are well known to one of ordinary skill in the art examples of which are described in U.S. Pat. Nos. 5,451,067, 6,679,242, 6,479,244, 6,472,185, 6,458,544, 6,440,707, and 6,312,902, which are herein incorporated by reference. If the alleles are present in equal numbers (as would be expected for a heterozygous locus), the allele ratio is 1 and there is no allele bias. As used herein, allele bias refers to a difference in the allele ratio for a pair of alleles from an allele ratio of 1. For alleles that do not have an even ratio (that is, a ratio of 1), allele bias can refer to a difference from the normal or expected allele ratio. Generally, the allele ratio for a locus in a heterozygous diploid sample will be 1, and this should be the allele ratio measurable in the unamplified sample. When a sample is amplified, uneven amplification can result in a bias in the allele ratio. Allele bias can be calculated, for example, as the difference between the allele ratio of alleles in an unamplified sample and the allele ratio for the same alleles in DNA amplified from the sample. This can be referred to as amplification allele bias. Amplification allele bias, when present, indicates that the ratio of alleles in the amplified DNA has been altered from the ratio in the original, unamplified genomic DNA. As an example, the allele ratio of two alleles of a locus that are present in equal number is 1. If the amplified DNA has a ratio of these two alleles of 0.5, then the amplification allele bias is 0.5 (calculated as 0.5/1=0.5). Such a bias can also be represented as 50% (referring to the difference in the ratios—0.5 is 50% of 1) or 2-fold (referring to the fold difference in the allele ratios—1 is twice as large as 0.5).

F. Amplified Nucleic Acid Quality

The disclosed method can result in replication of all or a substantial fraction of the nucleic acid molecules in a nucleic acid sample. As used herein, a substantial fraction of the nucleic acid molecules in a nucleic acid sample refers to 90% or more of the nucleic acid molecules (or nucleic acid sequences) present in the nucleic acid sample. As used herein, a significant fraction of the nucleic acid molecules in a nucleic acid sample refers to 50% or more of the nucleic acid molecules (or nucleic acid sequences) present in the nucleic acid sample. As used herein, a notable fraction of the nucleic acid molecules in a nucleic acid sample refers to 20% or more of the nucleic acid molecules (or nucleic acid sequences) present in the nucleic acid sample.

One measure of the quality of the amplified nucleic acids can be the percent representation, sequence representation, sequence representation bias, percent sequence representation, locus representation, locus representation bias, and/or percent locus representation in the amplified nucleic acids. A locus representation or sequence representation the same as or close to the locus or sequence representation in the source nucleic acid sample indicates amplified nucleic acids of the highest quality. Locus representation bias can refer to the ratio (usually expressed as a percentage) of the amount of a given locus in amplified nucleic acid to the amount of the same locus in the unamplified nucleic acid sample. In making this calculation, the measured amount of the locus in the amplified nucleic and the measured amount of the locus in the unamplified nucleic acid sample generally, can be normalized to the total amount of nucleic acid present in the amplified nucleic acid and the unamplified nucleic acid sample, respectively. Locus representation or locus representation bias expressed as a percentage (usually of a reference locus representation) can be referred to as a percent locus representation (which is a form of percent representation). Locus representation bias can also be expressed as the standard deviation of the locus representation in an amplified sample from the locus representation in the unamplified sample (or other reference locus representation). Locus representation bias can be a form of amplification bias. Locus representation can refer to the amount or level of a given locus (or a group of loci). Locus representation can be expressed as a locus representation relative to another, reference locus representation. Thus, for example, a percent locus representation is a form of locus representation.

Sequence representation bias can refer to the ratio (usually expressed as a percentage) of the amount of a given sequence in amplified nucleic acid to the amount of the same sequence in the unamplified nucleic acid sample. In making this calculation, the measured amount of the sequence in the amplified nucleic and the measured amount of the sequence in the unamplified nucleic acid sample generally can be normalized to the total amount of nucleic acid present in the amplified nucleic acid and the unamplified nucleic acid sample, respectively. Sequence representation or sequence representation bias expressed as a percentage (usually of a reference sequence representation) can be referred to as a percent sequence representation (which is a form of percent representation). Sequence representation bias can also be expressed as the standard deviation of the sequence representation in an amplified sample from the sequence representation in the unamplified sample (or other reference locus representation). Sequence representation bias can be a form of amplification bias. Sequence representation can refer to the amount or level of a given sequence (or a group of sequences). Sequence representation can be expressed as a sequence representation relative to another, reference sequence representation. Thus, for example, a percent sequence representation is a form of sequence representation.

Another measure of the quality of the amplified nucleic acids can be the amplification bias in the amplified nucleic acids. Amplification bias is the difference in the level of amplification of different sequences in a nucleic acid sample. A low amplification bias indicates amplified nucleic acids of the highest quality. One expression of amplification bias can be calculated as the ratio (usually expressed as a fold difference or a percent difference) of the locus representation bias of the locus having the highest locus representation bias to the locus representation bias having the lowest locus representation bias in the amplified nucleic acid. Another expression of amplification bias can be calculated as the ratio (usually expressed as a fold difference or a percent difference) of the locus representation of the locus having the highest locus representation to the locus representation having the lowest locus representation in the amplified nucleic acid. If sequence representation bias is measured, then amplification bias can be calculated as the ratio (usually expressed as a fold difference) of the sequence representation bias of the sequence having the highest sequence representation bias to the sequence representation bias having the lowest sequence representation bias in the amplified nucleic acid. Amplification bias can be calculated as the ratio (usually expressed as a fold difference) of the sequence representation of the sequence having the highest sequence representation to the sequence representation having the lowest sequence representation in the amplified nucleic acid. Although the above calculations are measures of amplification bias for all of the loci or sequences assessed, a subset of loci or sequences assessed can be used to calculate amplification bias. In fact, amplification bias can be calculated for individual loci, sequences or alleles. Thus, for example, amplification bias can also be calculated as the ratio (usually expressed as a fold difference or a percent difference) of the locus representation bias of one or more loci to the locus representation bias one or more other loci in the amplified nucleic acid. As another example, amplification bias can also be calculated as the ratio (usually expressed as a fold difference or a percent difference) of the locus representation in an unamplified sample of one or more loci to the locus representation in an amplified sample of the same loci.

G. Modifications and Additional Operations

1. Linear Strand Displacement Amplification

A modified form of multiple strand displacement amplification can be performed which results in linear amplification of a target sequence. This modified method is referred to as linear strand displacement amplification (LSDA) and is accomplished by using a set of primers where all of the primers are complementary to the same strand of the target sequence. In LSDA, as in MSDA, the set of primers hybridize to the target sequence and strand displacement amplification takes place. However, only one of the strands of the target sequence is replicated. LSDA requires thermal cycling between each round of replication to allow a new set of primers to hybridize to the target sequence. Such thermal cycling is similar to that used in PCR. Unlike linear, or single primer, PCR, however, each round of replication in LSDA results in multiple copies of the target sequence. One copy is made for each primer used. Thus, if 20 primers are used in LSDA, 20 copies of the target sequence will be made in each cycle of replication.

DNA amplified using MSDA and WGSDA can be further amplified by transcription. For this purpose, promoter sequences can be included in the non-complementary portion of primers used for strand displacement amplification, or in linker sequences used to concatenate DNA for MSDA-CD.

2. Reverse Transcription Multiple Displacement Amplification

Multiple displacement amplification can be performed on RNA or on DNA strands reverse transcribed from RNA. A useful form of the disclosed method, referred to as reverse transcription multiple displacement amplification (RT-MDA) involves reverse transcribing RNA, removal of the RNA (preferably by nuclease digestion using an RNA-specific nuclease such as RNAse H), and multiple displacement amplification of the reverse transcribed DNA. RT-MDA can be performed using either double-stranded cDNA or using just the first cDNA strand. In the latter case, the second cDNA strand need not be, and preferably is not, synthesized. RT-MDA is useful for quantitative analysis of mRNA or general amplification of mRNA sequences for any other purpose.

3. Repeat Multiple Displacement Amplification

The disclosed multiple displacement amplification operations can also be sequentially combined. For example, the product of MDA can itself be amplified in another multiple displacement amplification. This is referred to herein as repeat multiple displacement amplification (RMDA). This can be accomplished, for example, by diluting the replicated strands following MDA and subjecting them to a new MDA. This can be repeated one or more times. Each round of MDA will increase the amplification. Different forms of MDA, such as WGSDA and MSDA on particular target sequences can be combined. In general, repeat MDA can be accomplished by first bringing into contact a set of primers, DNA polymerase, and a target sample, and incubating the target sample under conditions that promote replication of the target sequence. Replication of the target sequence results in replicated strands, wherein during replication at least one of the replicated strands is displaced from the target sequence by strand displacement replication of another replicated strand; and then diluting the replicated strands, bringing into contact a set of primers, DNA polymerase, and the diluted replicated strands, and incubating the replicated strands under conditions that promote replication of the target sequence. Replication of the target sequence results in additional replicated strands, wherein during replication at least one of the additional replicated strands is displaced from the target sequence by strand displacement replication of another additional replicated strand. This form of the method can be extended by performing the following operation one or more times: diluting the additional replicated strands, bringing into contact a set of primers, DNA polymerase, and the diluted replicated strands, and incubating the replicated strands under conditions that promote replication of the target sequence. Replication of the target sequence results in additional replicated strands, wherein during replication at least one of the additional replicated strands is displaced from the target sequence by strand displacement replication of another additional replicated strand.

4. Using Products of Multiple Displacement Amplification

The nucleic acids produced using the disclosed method can be used for any purpose. For example, the amplified nucleic acids can be analyzed (such as by sequencing or probe hybridization) to determine characteristics of the amplified sequences or the presence or absence or certain sequences. The amplified nucleic acids can also be used as reagents for assays or other methods. For example, nucleic acids produced in the disclosed method can be coupled or adhered to a solid-state substrate. The resulting immobilized nucleic acids can be used as probes or indexes of sequences in a sample. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

Nucleic acids produced in the disclosed method also can be used as probes or hybridization partners. For example, sequences of interest can be amplified in the disclosed method and provide a ready source of probes. The replicated strands (produced in the disclosed method) can be cleaved prior to use as hybridization probes. For example, the replicated strands can be cleaved with DNAse I. The hybridization probes can be labeled as described elsewhere herein with respect to labeling of nucleic acids produce in the disclosed method.

Nucleic acids produced in the disclosed method also can be used for subtractive hybridization to identify sequences that are present in only one of a pair or set of samples. For example, amplified cDNA from different samples can be annealed and the resulting double-stranded material can be separated from single-stranded material. Unhybridized sequences would be indicative of sequences expressed in one of the samples but not others.

EXAMPLES

A. Example 1

Inconsistent Results with Large-Scale Random Primers

50 µL of Human Papillomavirus (HPV) plasmid was diluted using Negative Control media (50 mM $NaH_2PO_4$, 300 mM NaCl, 250 mM imidazole, pH 8.0). A half volume of 1× Denaturation Reagent (DNR) was added, and then quick shaken. Samples were then incubated for 15 minutes at room temperature.

Following denaturation, 25 µL of Probe Mix was added at room temperature to neutralize/hybridize the sample, then shaken to mix. The probe mix contained 0.2 ng/µL of each type (5 ng/assay of ddRNA/type) in 0.75×hc2 probe diluent.

Target enrichment was performed by capturing sequence specific RNA:DNA hybrids onto paramagnetic beads. The beads were modified with antibodies specific for RNA:DNA hybrids. The MAb paramagnetic beads were prepared by adding 10 μL of Protein G/MAb (2.5×10$^5$ beads/4) at room temperature, followed by incubation for 30 minutes at 65° C. with shaking.

After incubation, samples were placed on a 96-Well Magnetic-Ring Stand and allowed to stand for 2 minutes to form a pellet. The initial supernatant was aspirated by pipette. On each subsequent wash, a dump/blot wash was performed. Next, the beads were washed three times using 120 μL of hc2 Wash buffer with 0.05% Tween. The beads were washed one final time using 120 μL of reaction Wash buffer.

Isothermal amplification of the sample was performed by adding 20 μL of 1× Reaction Mix, which was then shaken to mix. The sample was then incubated for 1.5 hours at 30° C., and shaken to mix. The Reaction Mixes are shown below in Table 1.

Amplified sequences were detected using Luminex technology. For detection, 35% (7 μL) of sample was used for each reaction. For detection, 35% (7 μL) of sample was used for each reaction. The detection step of the assay began with denaturation in 10 μL of DNR (0.75×), followed by incubation for 15 minutes at 65° C. with shaking. Then, 10 μL of the RNA Probe Mix was added to hybridize/capture. The RNA Probe mix is a dilution of stock in Hybrid Capture 2 (HC2) PD (0.75×); 20 ng ddRNA/type, which is shaken to mix at room temperature. The oligonucleotides are each conjugated to 4 μL of Luminex beads at 750/μL (3000 beads per type/assay) in TE buffer. Next, the samples were incubated for 30 minutes at 65° C. with shaking at 1150 rpm, and then filtered through the 96-well filter plate without washing.

TABLE 1

Reaction Mix

| Reagents | Reaction Conc. (1X) | Stock | Stock Conc. (X) | Reaction Mix (μl) |
|---|---|---|---|---|
| Tris-HCl, pH 7.5 | 50 mM | 1M | 20 | 10.0 |
| MgCl$_2$ | 15 mM | 1M | 66.7 | 3.0 |
| (NH$_4$)$_2$ SO$_4$ | 10 mM | 1M | 100 | 2.0 |
| DTT | 4 mM | 0.1M | 25 | 8.0 |
| Purified BSA | 200 μg/ml | 10 mg/ml | 50 | 4.0 |
| dNTP | 1.6 mM total | 100 mM total | 62.5 | 3.2 |
| Primer | 250 μM | 10 mM | 40 | 5.0 |
| Phi29 | 1 U | 10 U/μl | 10 | 1.0 (*1 U phi29 per 20 μl RXN) |
| MBG H2O | N/A | N/A | N/A | 163.8 |
| | | | | 200 |

Amplified sequences were detected using Luminex technology. For detection, 35% (7 μL) of sample was used for each reaction. For detection, 35% (7 μL) of sample was used for each reaction. The detection step of the assay began with denaturation in 10 μL of DNR (0.75×), followed by incubation for 15 minutes at 65° C. with shaking. Then, 10 μL of the RNA Probe Mix was added to hybridize/capture. The RNA Probe mix is a dilution of stock in Hybrid Capture 2 (HC2) PD (0.75×); 20 ng ddRNA/type, which is shaken to mix at room temperature. The oligonucleotides are each conjugated to 4 μL of Luminex beads at 750/μL (3000 beads per type/assay) in TE buffer. Next, the samples were incubated for 30 minutes at 65° C. with shaking at 1150 rpm, and then filtered through the 96-well filter plate without washing.

The beads were then resuspended in 100 μL of 1× phosphate-buffered saline (PBS), 0.05% Tween-20, 10% goat serum and 10 ng of mouse monoclonal DNA:RNA hybrid-specific antibodies labeled with phycoerythrin (10 ng/assay). The samples were covered and incubated for 30 minutes at room temperature while shaking at 1150 rpm. The excess antibody was removed by filtration and the beads were resuspended in 100 μL PBS with 0.05% Tween-20. The samples were added and subsequently shaken on a 96-well filter plate for 1 minute. Finally, the samples were analyzed on the Luminex 100 analyzer (Luminex Corporation, Austin, Tex.) with a photomultiplier tube adjusted to 700 volts. One thousand copies of HPV 16 plasmid were analyzed. Median fluorescence intensity (MFI) values were calculated.

The results showed inconsistent amplification with large-scale (50 μmole) of random primers. This inconsistency is seen between lots produced by different vendors and among lots produced among the same vendor.

B. Example 2

Random Amplification with G-Deficient Primers Performs Comparably to Random Primers 50 μL of HPV 16 plasmid was diluted in TE buffer (10 mM Tris-Cl, pH 7.5, 1 mM EDTA) for each capture. To denature, 25 μL of 0.75× Denaturation Reagent was added and quick shaken. The sample was then incubated for 15 minutes at room temperature.

Following denaturation, 25 μL of Probe Mix was added at room temperature to neutralize/hybridize the sample, then shaken to mix. The probe mix contained 0.2 ng/μL of each type (5 ng/assay of ddRNA/type) in 0.75×hc2 probe diluent.

Target enrichment was performed by capturing sequence specific RNA:DNA hybrids onto paramagnetic beads. The beads were modified with antibodies specific for RNA:DNA hybrids. The MAb paramagnetic beads were prepared by adding 10 μL of Protein G/MAb (2.5×10$^5$ beads/μL) at room temperature, followed by incubation for 30 minutes at 65° C. with shaking.

After incubation, samples were placed on a 96-Well Magnetic-Ring Stand and allowed to stand for 2 minutes to form a pellet. The initial supernatant was aspirated by pipette. On each subsequent wash, a dump/blot wash was performed. Next, the beads were washed three times using 120 μL of hc2 Wash buffer with 0.05% Tween. The beads were washed one final time using 120 μL of reaction Wash buffer.

Isothermal amplification of the sample was performed by adding 20 μL of 1× Reaction Mix, which was then shaken to mix. The sample was then incubated for 1.5 hours at 30° C., and shaken to mix. The Reaction Mixes are shown below in Table 2.

Amplified sequences were subjected to no-filter detection using Luminex technology. For detection, 35% (7 μL) of sample was used for each reaction. The detection step of the assay began with denaturation in 10 μL of DNR (0.75×), followed by incubation for 15 minutes at 65° C. with shaking. Then, 10 μL of the RNA Probe Mix was added to hybridize/capture. The RNA Probe Mix is a dilution of stock in HC2 PD (0.75×); 20 ng ddRNA/type, which is shaken to mix at room temperature. The oligonucleotides are each conjugated to 10 μL of Luminex beads at 300/μL (3000 beads per type/assay) in TE buffer. The beads were then resuspended in 10 µL of 1× phosphate-buffered saline (PBS), 10% goat serum and mouse monoclonal DNA:RNA hybrid-specific antibodies labeled with phycoerythrin (PE-Ab) (40 ng/assay). Next, the samples were incubated for 30 minutes at 60° C. with shaking at 1150 rpm.

103 µL of water was added to each well (total volume of 150 µL). The samples were then added and subsequently shaken on a 96-well filter plate for 1 minute. Finally, the samples were analyzed on the Luminex 100 analyzer (Luminex Corporation, Austin, Tex.) with a photomultiplier tube adjusted to 700 volts. Median fluorescence intensity (MFI) values were calculated.

Detection on the Luminex showed that Random Amplification with G-deficient primers performs comparably to random primers. At 200 copies of HPV plasmid, a mix of 96-G-deficient primers produced the best results. At 1000 copies of HPV plasmid, a mix of 24- to 96-G-deficient primers performs comparably to random primers.

hybrids. The MAb paramagnetic beads were prepared by adding 10 µL of Protein G/MAb ($2.5 \times 10^5$ beads/µL) at room temperature, followed by incubation for 30 minutes at 65° C. with shaking.

After incubation, samples were placed on a 96-Well Magnetic-Ring Stand and allowed to stand for 2 minutes to form a pellet. The initial supernatant was aspirated by pipette. On each subsequent wash, a dump/blot wash was performed. Next, the beads were washed three times using 120 µL of hc2 Wash buffer with 0.05% Tween. The beads were washed one final time using 120 µL of reaction Wash buffer.

Isothermal amplification of the sample was performed by adding 20 µL of 1× Reaction Mix, which was then shaken to mix. The sample was then incubated for 2 hours at 30° C., and shaken to mix. The Reaction Mixes are shown below in Table 3.

TABLE 2

Reaction Mix

| Reagents | Reaction Conc. (1X) | Stock | Stock Conc. (X) | Random Amplification with Random Primers 250 µM Reaction Mix (µl) | Random Amplification with G-deficient primers 100 µM Reaction Mix (µl) |
|---|---|---|---|---|---|
| Tris-HCl, pH 7.5 | 50 mM | 1M | 20 | 20.0 | 20.0 |
| MgCl$_2$ | 15 mM | 1M | 66.7 | 6.0 | 6.0 |
| (NH$_4$)$_2$ SO$_4$ | 10 mM | 1M | 100 | 4.0 | 4.0 |
| DTT | 4 mM | 0.1M | 25 | 16.0 | 16.0 |
| Purified BSA | 200 µg/ml | 10 mg/ml | 50 | 8.0 | 8.0 |
| dNTP | 4 mM total | 100 mM total | 25 | 16.0 | 16.0 |
| Primer | See above | 10 mM | N/A | 10.0 | 6.0 |
| Phi29 | 1 U | 10 U/µl | 10 | 2.0 (*1 U phi29 per 20 µl RXN) | 2.0 (*1 U phi29 per 20 µl RXN) |
| MBG H2O | N/A | N/A | N/A | 318.0 | 322.0 |
| | | | | 400 | 400 |

C. Example 3

Detection of HPV, GC, and CT with G-Deficient Primers

50 µL of GC and CT plasmids were diluted in TE buffer (10 mM Tris-Cl, pH 7.5, 1 mM EDTA) for each capture. To denature, 25 µL of 0.75× Denaturation Reagent was added and quick shaken. The sample was then incubated for 15 minutes at room temperature.

Following denaturation, 25 µL of Probe Mix was added at room temperature to neutralize/hybridize the sample, then shaken to mix. The probe mix contained 0.2 ng/µL of each type (5 ng/assay of ddRNA/type) in 0.75×hc2 probe diluent.

Target enrichment was performed by capturing sequence specific RNA:DNA hybrids onto paramagnetic beads. The beads were modified with antibodies specific for RNA:DNA Amplified sequences were subjected to no-filter detection using Luminex technology. For detection, 35% (7 µL) of sample was used for each reaction. The detection step of the assay began with denaturation in 10 µL of 0.5M NaOH, followed by incubation for 15 minutes at 60° C. with shaking. Then, 10 µL of the RNA Probe Mix was added to hybridize/capture. The RNA Probe Mix is a dilution of stock in HC2 PD (0.75×); 20 ng ddRNA/type, which is shaken to mix at room temperature. The oligonucleotides are each conjugated to 10 µL of Luminex beads at 300/µL (3000 beads per type/assay) in TE buffer. The beads were then resuspended in 10 µL of 1× phosphate-buffered saline (PBS), 10% goat serum and mouse monoclonal DNA:RNA hybrid-specific antibodies labeled with phycoerythrin (PE-Ab) (40 ng/assay). Next, the samples were incubated for 30 minutes at 60° C. with shaking at 1150 rpm.

TABLE 3

| | | | | 1 Target Mix 100 μM | 2 Target Mix 100 μM |
| Reagents | Reaction Conc. (1X) | Stock | Stock Conc. (X) | Reaction Mix (μl) | Reaction Mix (μl) |
|---|---|---|---|---|---|
| Tris-HCl, pH 7.5 | 50 mM | 1M | 20 | 30.0 | 30.0 |
| MgCl$_2$ | 15 mM | 1M | 66.7 | 9.0 | 9.0 |
| (NH$_4$)$_2$ SO$_4$ | 10 mM | 1M | 100 | 6.0 | 6.0 |
| DTT | 4 mM | 0.1M | 25 | 24.0 | 24.0 |
| Purified BSA | 200 μg/ml | 10 mg/ml | 50 | 12.0 | 12.0 |
| dNTP | 4 mM total | 100 mM total | 25 | 24.0 | 24.0 |
| G-Deficient Primers | See above | 10 mM | N/A | 6.0 | 12.0 |
| Phi29 | 1 U | 10 U/μl | 10 | 3.0 (*1 U phi29 per 20 μl RXN) | 3.0 (*1 U phi29 per 20 μl RXN) |
| MBG H2O | N/A | N/A | N/A | 486.0 | 480.0 |
| | | | | 600 | 600 |

103 μL of water was added to each well (total volume of 150 μL). The samples were then added and subsequently shaken on a 96-well filter plate for 1 minute. Finally, the samples were analyzed on the Luminex 100 analyzer (Luminex Corporation, Austin, Tex.) with a photomultiplier tube adjusted to 700 volts. Median fluorescence intensity (MFI) values were calculated.

Detection on the Luminex showed that in addition to HPV targets, G-deficient primers can also be used to amplify CT and GC targets. The results (See Table 4) further demonstrated that amplification of CT and GC G-deficient primers (24-mix) perform comparably with a random primer mix.

TABLE 4

| Target | Primer | MFI |
|---|---|---|
| CT | Random | 6328 |
| CT | CT-bias | 6727 |
| CT | GC-bias | 1813 |
| CT | CT/GC-bias | 7091 |
| GC | Random | 13999 |
| GC | CT-bias | 7785 |
| GC | GC-bias | 10748 |
| GC | CT/GC-bias | 11444 |

D. Example 4

Efficient Amplification Illustrated with G-Deficient Primer Mixes of 48-144 Specific Sequences 50 μL of HPV 16 plasmid was diluted in TE buffer (10 mM Tris-Cl, pH 7.5, 1 mM EDTA) for each capture. To denature, 25 μL of 0.5M NaOH was added and quick shaken. The sample was then incubated for 15 minutes at 50° C.

Following denaturation, 25 μL of Probe Mix was added at room temperature to neutralize/hybridize the sample, then shaken to mix. The probe mix contained 0.2 ng/μL of each type (5 ng/assay of ddRNA/type) in 0.75×hc2 probe diluent.

Target enrichment was performed by capturing sequence specific RNA:DNA hybrids onto paramagnetic beads. The beads were modified with antibodies specific for RNA:DNA hybrids. For hybrid capture 10 μL of Protein G/MAb beads (2.5×10$^5$ beads/4) were added to hybridization mixture at room temperature, followed by incubation for 30 minutes at 60° C. with shaking.

After incubation, samples were placed on a 96-Well Magnetic-Ring Stand and allowed to stand for 2 minutes to form a pellet. The initial supernatant was aspirated by pipette. On each subsequent wash, a dump/blot wash was performed. Next, the beads were washed three times using 120 μL of hc2 Wash buffer with 0.05% Tween. The beads were washed one final time using 120 μL of reaction Wash buffer.

Isothermal amplification of the sample was performed by adding 20 μL of 1× Reaction Mix, which was then shaken to mix. The sample was then incubated for 1.5 hours at 30° C., and shaken to mix. The Reaction Mixes are shown below in Table 5.

Amplified sequences were subjected to no-filter detection using Luminex technology. For detection, 35% (7 μL) of sample was used for each reaction. The detection step of the assay began with denaturation in 10 μL of BE-DNR (0.75×), followed by incubation for 15 minutes at 60° C. with shaking. Then, 10 μL of the RNA Probe Mix was added to hybridize/capture. The RNA Probe Mix is a dilution of stock in HC2 PD (0.75×); 20 ng ddRNA/type, which is shaken to mix at room temperature. The oligonucleotides are each conjugated to 10 μL of Luminex beads at 300/μL (3000 beads per type/assay) in TE buffer. The beads were then resuspended in 10 μL of 1× phosphate-buffered saline (PBS), 10% goat serum and mouse monoclonal DNA:RNA hybrid-specific antibodies labeled with phycoerythrin (PE-Ab) (40 ng/assay). Next, the samples were incubated for 30 minutes at 60° C. with shaking at 1150 rpm.

103 μL of water was added to each well (total volume of 150 μL). The samples were then added and subsequently shaken on a 96-well filter plate for 1 minute. Finally, the samples were analyzed on the Luminex 100 analyzer (Luminex Corporation, Austin, Tex.) at a default photomultiplier tube setting. Median fluorescence intensity (MFI) values were calculated.

Detection on the Luminex showed efficient amplification with G-Deficient Primer mixes of 48 to 144 specific sequences. The results further demonstrated that eliminating possible problematic primer sequences (G-rich) leads to more consistent and robust amplification.

TABLE 5

Reaction Mix

| Reagents | Reaction Conc. (1X) | Stock | Stock Conc. (X) | Random Amplification Random Primers 250 μM Reaction Mix (μl) | Random Amplification G-Deficient Primers 100 μM Reaction Mix (μl) |
|---|---|---|---|---|---|
| Tris-HCl, pH 7.5 | 50 mM | 1M | 20 | 10.0 | 10.0 |
| MgCl$_2$ | 15 mM | 1M | 66.7 | 3.0 | 3.0 |
| (NH$_4$)$_2$SO$_4$ | 10 mM | 1M | 100 | 2.0 | 2.0 |
| DTT | 4 mM | 0.1M | 25 | 8.0 | 8.0 |
| Purified BSA | 200 μg/ml | 10 mg/ml | 50 | 4.0 | 4.0 |
| dNTP | 4 mM total | 100 mM total | 25 | 8.0 | 8.0 |
| Primer | See above | 10 mM | N/A | 5.0 | 3.0 |
| Phi29 | 1 U | 10 U/μl | 10 | 1.0 (*1 U phi29 per 20 μl RXN) | 1.0 (*1 U phi29 per 20 μl RXN) |
| MBG H2O | N/A | N/A | N/A | 159.0 | 161.0 |
| | | | | 200 | 200 |

E. Example 5

Optimized Concentration of G-Deficient Primers

50 μL of HPV 16 plasmid was diluted in TE buffer (10 mM Tris-Cl, pH 7.5, 1 mM EDTA) for each capture. To denature, 25 μL of 0.75×FE-Denaturation Reagent was added and quick shaken. The sample was then incubated for 15 minutes at 50° C. with shaking.

Following denaturation, 25 μL of Probe Mix was added at room temperature to neutralize/hybridize the sample, then shaken to mix. The probe mix contained 0.2 ng/μL of each type (5 ng/assay of ddRNA/type) in 0.75×hc2 probe diluent.

Target enrichment was performed by capturing sequence specific RNA:DNA hybrids onto paramagnetic beads. The beads were modified with antibodies specific for RNA:DNA hybrids. The MAb paramagnetic beads were prepared by adding 10 μL of Protein G/MAb (2.5×10$^5$ beads/μL) at room temperature, followed by incubation in FE for 30 minutes at 60° C. with shaking.

After incubation, samples were placed on a 96-Well Magnetic-Ring Stand and allowed to stand for 2 minutes to form a pellet. The initial supernatant was aspirated by pipette. On each subsequent wash, a dump/blot wash was performed. Next, the beads were washed three times using 120 μL of hc2 Wash buffer with 0.05% Tween. The beads were washed one final time using 120λ of reaction Wash buffer.

Isothermal amplification of the sample was performed by adding 20 μL of 1× Reaction Mix, which was then shaken to mix. The sample was then incubated for 2 hours at 30° C., and shaken to mix. The Reaction Mixes are shown below in Tables 6 and 7.

Amplified sequences were subjected to no-filter detection using Luminex technology. For detection, 35% (7 μL) of sample was used for each reaction. The detection step of the assay began with denaturation in 10 μL of BE-DNR (0.75×), followed by incubation for 15 minutes at 60° C. with shaking. Then, 10 μL of the RNA Probe Mix was added to hybridize/capture. The RNA Probe Mix is a dilution of stock in HC2 PD (0.75×); 20 ng ddRNA/type, which is shaken to mix at room temperature. The oligonucleotides are each conjugated to 10 μL of Luminex beads at 300/μL (3000 beads per type/assay) in TE buffer. The beads were then resuspended in 10 μL of 1× phosphate-buffered saline (PBS), 10% goat serum and mouse monoclonal DNA:RNA hybrid-specific antibodies labeled with phycoerythrin (PE-Ab) (40 ng/assay). Next, the samples were incubated for 30 minutes at 60° C. with shaking at 1150 rpm.

103 μL of water was added to each well (total volume of 150 μL). The samples were then added and subsequently shaken on a 96-well filter plate for 1 minute. Finally, the samples were analyzed on the Luminex 100 analyzer (Luminex Corporation, Austin, Tex.) at a default photomultiplier tube setting. Median fluorescence intensity (MFI) values were calculated.

Detection on the Luminex showed that for both a 48- or 96-G-Deficient Primer mix, the optimal primer concentrations were between 150-250 μM. Yet, comparable results were also obtained from the 96-G-Deficient Primer mix using as little as 50 μM. The results further demonstrated that too much primer (>350 μM) decreases amplification efficiency.

TABLE 6

Reaction Mix

| Reagents | Reaction Conc. (1X) | Stock | Stock Conc. (X) | G-Deficient Primer 50 μM Reaction Mix (μl) | G-Deficient Primer 150 μM Reaction Mix (μl) | G-Deficient Primer 250 μM Reaction Mix (μl) |
|---|---|---|---|---|---|---|
| Tris-HCl, pH 7.5 | 50 mM | 1M | 20 | 20.0 | 20.0 | 20.0 |

TABLE 6-continued

Reaction Mix

| Reagents | Reaction Conc. (1X) | Stock | Stock Conc. (X) | G-Deficient Primer 50 μM Reaction Mix (μl) | G-Deficient Primer 150 μM Reaction Mix (μl) | G-Deficient Primer 250 μM Reaction Mix (μl) |
|---|---|---|---|---|---|---|
| MgCl$_2$ | 15 mM | 1M | 66.7 | 6.0 | 6.0 | 6.0 |
| (NH$_4$)$_2$SO$_4$ | 10 mM | 1M | 100 | 4.0 | 4.0 | 4.0 |
| DTT | 4 mM | 0.1M | 25 | 16.0 | 16.0 | 16.0 |
| Purified BSA | 200 μg/ml | 10 mg/ml | 50 | 8.0 | 8.0 | 8.0 |
| dNTP | 4 mM total | 100 mM total | 25 | 16.0 | 16.0 | 16.0 |
| Primer | See above | 10 mM | N/A | 2.0 | 6.0 | 10.0 |
| Phi29 | 1U | 10 U/μl | 10 | 2.0 (*1U phi29 per 20 μl RXN) | 2.0 (*1U phi29 per 20 μl RXN) | 2.0 (*1U phi29 per 20 μl RXN) |
| MBG H$_2$O | N/A | N/A | N/A | 326.0 | 322.0 | 318.0 |
| | | | | 400 | 400 | 400 |

TABLE 7

Reaction Mix

| Reagents | Reaction Conc. (1X) | Stock | Stock Conc. (X) | G-Deficient Primer 150 μM Reaction Mix (μl) | G-Deficient Primer 250 μM Reaction Mix (μl) | G-Deficient Primer. 350 μM Reaction Mix (μl) |
|---|---|---|---|---|---|---|
| 1.5X Master Mix | 1X | 1.5X | 1.5 | 266.7 | 266.7 | 266.7 |
| Primer | See above | 10 mM | N/A | 6.0 | 10.0 | 14.0 |
| Phi29 | 1U | 10 U/μl | 10 | 2.0 (*1U phi29 per 20 μl RXN) | 2.0 (*1U phi29 per 20 μl RXN) | 2.0 (*1U phi29 per 20 μl RXN) |
| MBG H$_2$O | N/A | N/A | N/A | 125.3 | 121.3 | 117.3 |
| | | | | 400 | 400 | 400 |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. An in vitro method of randomly amplifying a target nucleic acid sequence, the method comprising, bringing into contact a DNA polymerase, a target sample, and a set of random G-deficient primers, and incubating the target sample under conditions that promote replication of the target sequence, wherein replication of the target sequence results in replicated strands, wherein all of the primers of the primer set:
   a. are exonuclease-resistant,
   b. have at least one guanine residue,
   c. do not contain two or more consecutive guanine residues at the 3' end, and
   d. do not comprise three or more consecutive guanine residues.

2. The method of claim 1, wherein at least one of the replicated strands is displaced from the target sequence by strand displacement replication of another replicated strand.

3. The method of claim 1, wherein the target sample is not subjected to denaturing conditions.

4. The method of claim 1, wherein the primers each contain at least one modified nucleotide.

5. The method of claim 4, wherein the at least one modified nucleotide renders the primers resistant to 3'-5' exonuclease.

6. The method of claim 1, wherein the target sample is not subjected to heat denaturing conditions.

7. The method of claim wherein the conditions that promote replication of the target sequence are substantially isothermic.

8. The method of claim 1, wherein the conditions that promote replication of the target sequence involve thermal cycling.

9. The method of claim further comprising:
diluting the replicated strands, contacting the diluted replicated strands with a second set of primers and DNA polymerase, and incubating the replicated strands under conditions that promote replication of the target sequence,
wherein replication of the target sequence results in additional replicated strands, wherein during replication at least one of the additional replicated strands is displaced from the target sequence by strand displacement replication of another additional replicated strand.

10. The method of claim 9, wherein the primers of the second set of primers are random G-deficient primers.

11. A method of randomly amplifying a target nucleic acid sequence, the method comprising, bringing into contact a DNA polymerase, a target sample, and a set of random G-deficient primers, and incubating the target sample under conditions that promote replication of the target sequence, wherein nucleic acids in the target sample are not separated from other material in the target sample, wherein all of the primers of the primer set:
a. are exonuclease-resistant,
b. have at least one guanine residue,
c. do not contain two or more consecutive guanine residues at the 3' end, and
d. do not comprise three or more consecutive guanine residues.

12. The method of claim 11, wherein the target sample is a crude cell lysate.

13. The method of claim 11, wherein replication of the target sequence results in replicated strands, wherein during replication at least one of the replicated strands is displaced from the target sequence by strand displacement replication of another replicated strand.

14. A method of randomly amplifying messenger RNA, the method comprising,
reverse transcribing messenger RNA to produce a first strand cDNA,
bringing into contact a set of random G-deficient primers, DNA polymerase, and the first strand cDNA, and incubating under conditions that promote replication of the first strand cDNA,
wherein replication of the first strand cDNA results in replicated strands, wherein during replication at least one of the replicated strands is displaced from the first strand cDNA by strand displacement replication of another replicated strand, and wherein all of the primers of the primer set:
a. are exonuclease-resistant,
b. have at least one guanine residue,
c. do not contain two or more consecutive guanine residues at the 3' end, and
d. do not comprise three or more consecutive guanine residues.

15. A method of randomly amplifying a target nucleic acid sequence, the method comprising,
(a) mixing a set of random G-deficient primers with a target sample, to produce a primer-target sample mixture, and incubating the primer-target sample mixture under conditions that promote hybridization between the random G-deficient primers and the target sequence in the primer-target sample mixture, wherein all of the primers of the primer set are exonuclease-resistant, have at least one guanine residue, do not contain two or more consecutive guanine residues at the 3' end, and do not comprise three or more consecutive guanine residues; and
(b) mixing DNA polymerase with the primer-target sample mixture, to produce a polymerase-target sample mixture, and incubating the polymerase-target sample mixture under conditions that promote replication of the target sequence,
wherein replication of the target sequence results in replicated strands, wherein during replication at least one of the replicated strands is displaced from the target sequence by strand displacement replication of another replicated strand, wherein the target sequence is a nucleic acid sample of substantial complexity.

16. The method of claim 15, further comprising the step of:
(c) thermal cycling to allow hybridization between the random G-deficient primers and the replicated strands, and incubating under conditions that promote replication of the target sequence and replicated strands.

17. The method of claim 15, wherein the conditions that promote replication of the target sequence are substantially isothermic.

18. The method of claim 15, wherein the conditions that promote replication of the target sequence involve thermal cycling.

19. The method of claim 1, wherein the set of primers comprises three or more primers.

20. The method of claim 19, wherein each of the three or more primers has a different sequence.

21. A kit comprising a lysis solution, a stabilization solution, a DNA polymerase, and a set of random G-deficient primers, wherein all of the primers of the primer set:
a. are exonuclease-resistant,
b. have at least one guanine residue,
c. do not contain two or more consecutive guanine residues at the 3' end, and
d. do not comprise three or more consecutive guanine residues.

22. The kit of claim 21, further comprising deoxynucleotide triphosphates.

23. The kit of claim 21, further comprising one or more detection probes.

* * * * *